US012417589B2

(12) United States Patent
Hsu et al.

(10) Patent No.: US 12,417,589 B2
(45) Date of Patent: Sep. 16, 2025

(54) CREATING SCENT MODELS AND USING SCENT MODELS IN CROSS-REALITY ENVIRONMENTS

(71) Applicant: AT&T Intellectual Property I, L.P., Atlanta, GA (US)

(72) Inventors: Wen-Ling Hsu, Bridgewater, NJ (US); Eric Zavesky, Austin, TX (US); Louis Alexander, Franklin, NJ (US); Aritra Guha, Edison, NJ (US); Jean-Francois Paiement, Palm Desert, CA (US); Qiong Wu, Bridgewater, NJ (US); Zhengyi Zhou, Chappaqua, NY (US)

(73) Assignee: AT&T Intellectual Property I, L.P., Atlanta, GA (US)

( * ) Notice: Subject to any disclaimer, the term of this patent is extended or adjusted under 35 U.S.C. 154(b) by 313 days.

(21) Appl. No.: 17/951,185

(22) Filed: Sep. 23, 2022

(65) Prior Publication Data
US 2024/0104858 A1    Mar. 28, 2024

(51) Int. Cl.
*G06T 19/00*    (2011.01)
*A61L 9/12*    (2006.01)

(52) U.S. Cl.
CPC ........... *G06T 19/006* (2013.01); *A61L 9/125* (2013.01)

(58) Field of Classification Search
CPC .............................. G06T 19/006; A61L 9/125
USPC ....................................................... 345/419
See application file for complete search history.

(56) References Cited

U.S. PATENT DOCUMENTS

| 2015/0243068 | A1* | 8/2015 | Solomon | G02B 27/017 |
| | | | | 345/419 |
| 2017/0315103 | A1* | 11/2017 | Biswas | G01N 33/0075 |
| 2020/0132999 | A1* | 4/2020 | Choi | G06F 18/214 |
| 2020/0330860 | A1* | 10/2020 | Flego | B05B 7/2416 |
| 2021/0001214 | A1* | 1/2021 | Flego | A63F 13/52 |
| 2022/0379200 | A1* | 12/2022 | Wisniewski | G06F 3/01 |

OTHER PUBLICATIONS

University of Tokyo, Public Relations Office, Press Release, "Seeing how odor is processed in the brain; New study shows odor unpleasantness processed more quickly than perceived quality," May 27, 2022, retrieved at https://www.u-tokyo.ac.jp/focus/en/press/z0508_00222.html on Sep. 5, 2022.

(Continued)

*Primary Examiner* — Thomas J Lett
(74) *Attorney, Agent, or Firm* — Hartman & Citrin LLC

(57) ABSTRACT

Creating scent models and using scent models in cross-reality environments can include capturing experience data identifying a scent detected and a context in which the scent was detected. The experience data can be provided to a scent modeling service to generate a scent model that can represent perceived scents and perceived scent intensities for a user. The scent model can be used to generate cross-reality session data to be used in a cross-reality session presented by a cross-reality device. The cross-reality device can include a scent generator and can generate the cross-reality session using data obtained from the user device. The cross-reality device can generate a further scent during the cross-reality session based on the scent model.

20 Claims, 9 Drawing Sheets

(56) References Cited

OTHER PUBLICATIONS

Stub, Zev, "Moodify: The Israeli company working to create an online scent experience," The Jerusalem Post, Oct. 4, 2021, retrieved at https://www.jpost.com/jpost-tech/moodify-the-israeli-company-working-to-create-an-online-scent-experience-680978 on Sep. 5, 2022.
Jeffay, Nathan, "Digitizing odors: Israelis whiff the future with 'smellophone' tech breakthrough," The Times of Israel, Nov. 11, 2020, retrieved at https://www.timesofisrael.com/digitizing-odors-israelis-whiff-future-with-smellophone-tech-breakthrough/ on Sep. 5, 2022.
Pratt et al., U.S. Appl. No. 17/218,704, filed Mar. 31, 2021.
Schuman, Evan, "The game-changing potential of smartphones that can smell," Computerworld, Jun. 6, 2018, retrieved at https://www.computerworld.com/article/3278594/the-game-changing-potential-of-smartphones-that-can-smell.html on Mar. 9, 2021.

\* cited by examiner

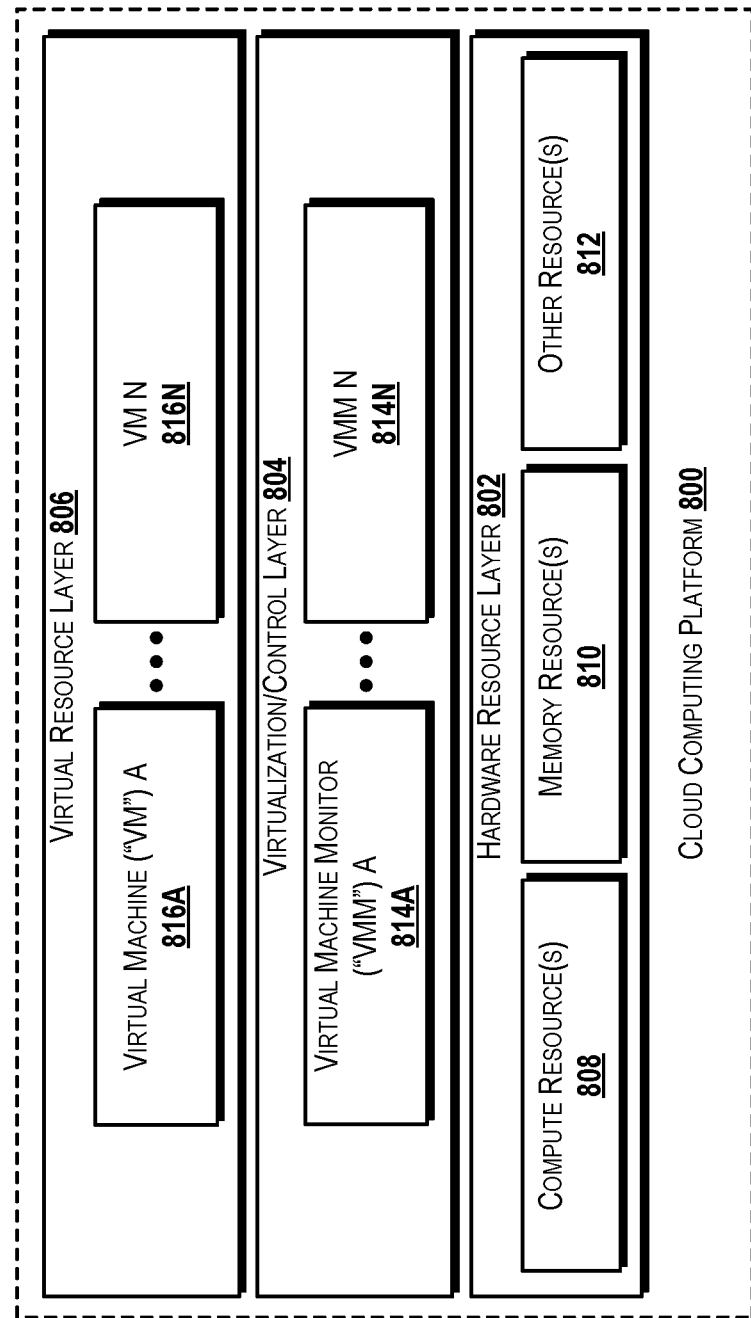

CREATING SCENT MODELS AND USING SCENT MODELS IN CROSS-REALITY ENVIRONMENTS

BACKGROUND

Virtual reality, augmented reality, and/or cross-reality immersions have become more frequently and widely used. As technology has improved, the realism of certain experiences has increased. For example, the rendering capabilities of computing devices has enabled the presentation of environments in a continually increasing level of detail. The improving rendering capabilities of computers, as well as other advances, have made virtual reality, augmented reality, and/or cross-reality immersions more realistic than what was previously possible.

One of the strongest senses in human beings is the sense of smell. In fact, some memories and/or other emotions can be triggered by certain scents. Smell, however, is a sense that typically is not well-served in virtual reality, augmented reality, and/or cross-reality immersions. While some technology exists for electronically sensing and/or electronically generating scents, such technologies are typically based on and/or employ a generic bank of scents that can be applied as directed by the creator of a virtual reality, augmented reality, and/or cross-reality environment.

SUMMARY

The present disclosure is directed to creating scent models and using scent models in cross-reality environments. A user device can be associated with a user. The user device can execute a scent module or the scent module can be included as part of a cross-reality application. The scent module can be configured to capture one or more scents (e.g., using the scent sensors) at various times, as well as various other information associated with the scent experience such as a geographic location at which the scent experience occurred, context associated with the scent experience (e.g., what the user and/or user device were doing when the scent experience occurred), user data that identifies the user and/or user device, history and/or preferences associated with the scents detected by the user device, combinations thereof, or the like. These and/or other information can be captured by the user device and provided to the scent modeling service for use in generating a scent model.

The scent modeling service can analyze one or more releases of the experience data to generate and/or update the scent model. The scent model can include a data structure that can define for a user, user device, cross-reality device, other entity and/or device, combinations thereof, or the like, various aspects of scents and/or smelling such as levels of sensitivity the user has for one or more scents, indication as to how long it takes a user to smell particular scents, preferences associated with the user for scents, contexts in which scents have been detected and/or indications as to how context may impact scent detection by the user, what scents should or should not be used, feedback relating to scent as obtained from the user, combinations thereof, or the like. The scent modeling service can store the scent model and/or can provide the scent model to the user device.

The cross-reality application can use the scent model to generate and/or optimize scent experiences in cross-reality sessions for the user. Thus, the cross-reality application can use the scent model to determine scents to emit using the scent generator, when to emit the scents using the scent generator, intensities of the scents to be emitted using the scent generator, timing (e.g., lead time, duration, linger time, etc.) of the scent emissions using the scent generator, combinations thereof, or the like. Thus, the scent model can be used to personalize the scent experience associated with the cross-reality device, thereby enhancing the use of scent in cross-reality sessions for the user. It should be understood that this example is illustrative, and therefore should not be construed as being limiting in any way.

According to one aspect of the concepts and technologies disclosed herein, a system is disclosed. The system can include a processor and a memory. The memory can store computer-executable instructions that, when executed by the processor, cause the processor to perform operations. The operations can include capturing, at a user device including a scent sensor, experience data including a scent detected using the scent sensor and context data that can define a context in which the scent was detected, and providing, to a scent modeling service, the experience data. The scent modeling service can generate a scent model associated with a user of the user device based on the experience data, the scent model representing perceived scents and perceived scent intensities associated with the user. The operations further can include obtaining, from the scent modeling service, the scent model, and using the scent model to generate cross-reality session data. The cross-reality session data can be used in a cross-reality session that can be presented by a cross-reality device. The cross-reality device can include a scent generator and the cross-reality device can generate the cross-reality session using the cross-reality session data obtained from the user device. The cross-reality device can generate a further scent during the cross-reality session based on the scent model.

In some embodiments, the computer-executable instructions, when executed by the processor, can cause the processor to perform operations that further can include obtaining feedback relating to the further scent that was generated during the cross-reality session and in response to a determination that the scent model is to be updated based on the feedback, sending, to the scent modeling service, feedback data that describes the feedback; and receiving, from the scent modeling service, an updated scent model. In some embodiments, the experience data further can include test data that can define two or more scents detected during a scent test. The test data also can define, for each of the two or more scents, an identification of the respective scent and an intensity of the respective scent.

In some embodiments, the context data can define a geographical location at which the scent was detected. In some embodiments, the context data further can define an activity associated with the user device when the scent was detected. In some embodiments, the experience data further can include preference data that can define user likes and dislikes. The preference data can define a first set, group, or list of two or more scents that should not be presented in the cross-reality session and a second set, group, or list of two or more scents that should be presented in the cross-reality session. In some embodiments, the scent model can include a data structure that can define two or more scents and two or more scent intensities, wherein the scent intensities are defined in parts per million.

According to another aspect of the concepts and technologies disclosed herein, a method is disclosed. The method can include capturing, at a user device including a processor and a scent sensor, experience data including a scent detected using the scent sensor and context data that can define a context in which the scent was detected; and providing, by the processor and to a scent modeling service, the experience data. The scent modeling service can generate a scent model associated with a user of the user device based on the experience data, the scent model representing perceived scents and perceived scent intensities associated with the user. The method further can include obtaining, by the processor and from the scent modeling service, the scent model, and using, by the processor, the scent model to generate cross-reality session data. The cross-reality session data can be used in a cross-reality session that can be presented by a cross-reality device. The cross-reality device can include a scent generator and the cross-reality device can generate the cross-reality session using the cross-reality session data obtained from the user device. The cross-reality device can generate a further scent during the cross-reality session based on the scent model.

In some embodiments, the method can further include obtaining feedback relating to the further scent that was generated during the cross-reality session and in response to a determination that the scent model is to be updated based on the feedback, sending, to the scent modeling service, feedback data that describes the feedback, and receiving, from the scent modeling service, an updated scent model. In some embodiments, the experience data further can include test data that can define two or more scents detected during a scent test. The test data also can define, for each of the two or more scents, an identification of the respective scent and an intensity of the respective scent.

In some embodiments, the context data can define a geographical location at which the scent was detected. In some embodiments, the context data further can define an activity associated with the user device when the scent was detected. In some embodiments, the experience data further can include preference data that can define user likes and dislikes. The preference data can define a first set, group, or list of two or more scents that should not be presented in the cross-reality session and a second set, group, or list of two or more scents that should be presented in the cross-reality session. In some embodiments, the scent model can include a data structure that can define two or more scents and two or more scent intensities, wherein the scent intensities are defined in parts per million.

According to yet another aspect of the concepts and technologies disclosed herein, a computer storage medium is disclosed. The computer storage medium can store computer-executable instructions that, when executed by a processor, cause the processor to perform operations. The operations can include capturing, at a user device including a scent sensor, experience data including a scent detected using the scent sensor and context data that can define a context in which the scent was detected, and providing, to a scent modeling service, the experience data. The scent modeling service can generate a scent model associated with a user of the user device based on the experience data, the scent model representing perceived scents and perceived scent intensities associated with the user. The operations further can include obtaining, from the scent modeling service, the scent model, and using the scent model to generate cross-reality session data. The cross-reality session data can be used in a cross-reality session that can be presented by a cross-reality device. The cross-reality device can include a scent generator and the cross-reality device can generate the cross-reality session using the cross-reality session data obtained from the user device. The cross-reality device can generate a further scent during the cross-reality session based on the scent model.

In some embodiments, the computer-executable instructions, when executed by the processor, can cause the processor to perform operations that further can include obtaining feedback relating to the further scent that was generated during the cross-reality session and in response to a determination that the scent model is to be updated based on the feedback, sending, to the scent modeling service, feedback data that describes the feedback, and receiving, from the scent modeling service, an updated scent model. In some embodiments, the experience data further can include test data that can define two or more scents detected during a scent test. The test data also can define, for each of the two or more scents, an identification of the respective scent and an intensity of the respective scent.

In some embodiments, the context data can define a geographical location at which the scent was detected. In some embodiments, the context data further can define an activity associated with the user device when the scent was detected. In some embodiments, the experience data further can include preference data that can define user likes and dislikes. The preference data can define a first set, group, or list of two or more scents that should not be presented in the cross-reality session and a second set, group, or list of two or more scents that should be presented in the cross-reality session. In some embodiments, the scent model can include a data structure that can define two or more scents and two or more scent intensities, wherein the scent intensities are defined in parts per million.

Other systems, methods, and/or computer program products according to embodiments will be or become apparent to one with skill in the art upon review of the following drawings and detailed description. It is intended that all such additional systems, methods, and/or computer program products be included within this description and be within the scope of this disclosure.

BRIEF DESCRIPTION OF THE DRAWINGS

FIG. 8 is a diagram illustrating a computing environment capable of implementing aspects of the concepts and technologies disclosed herein, according to some illustrative embodiments of the concepts and technologies described herein.

DETAILED DESCRIPTION

Figure 1:
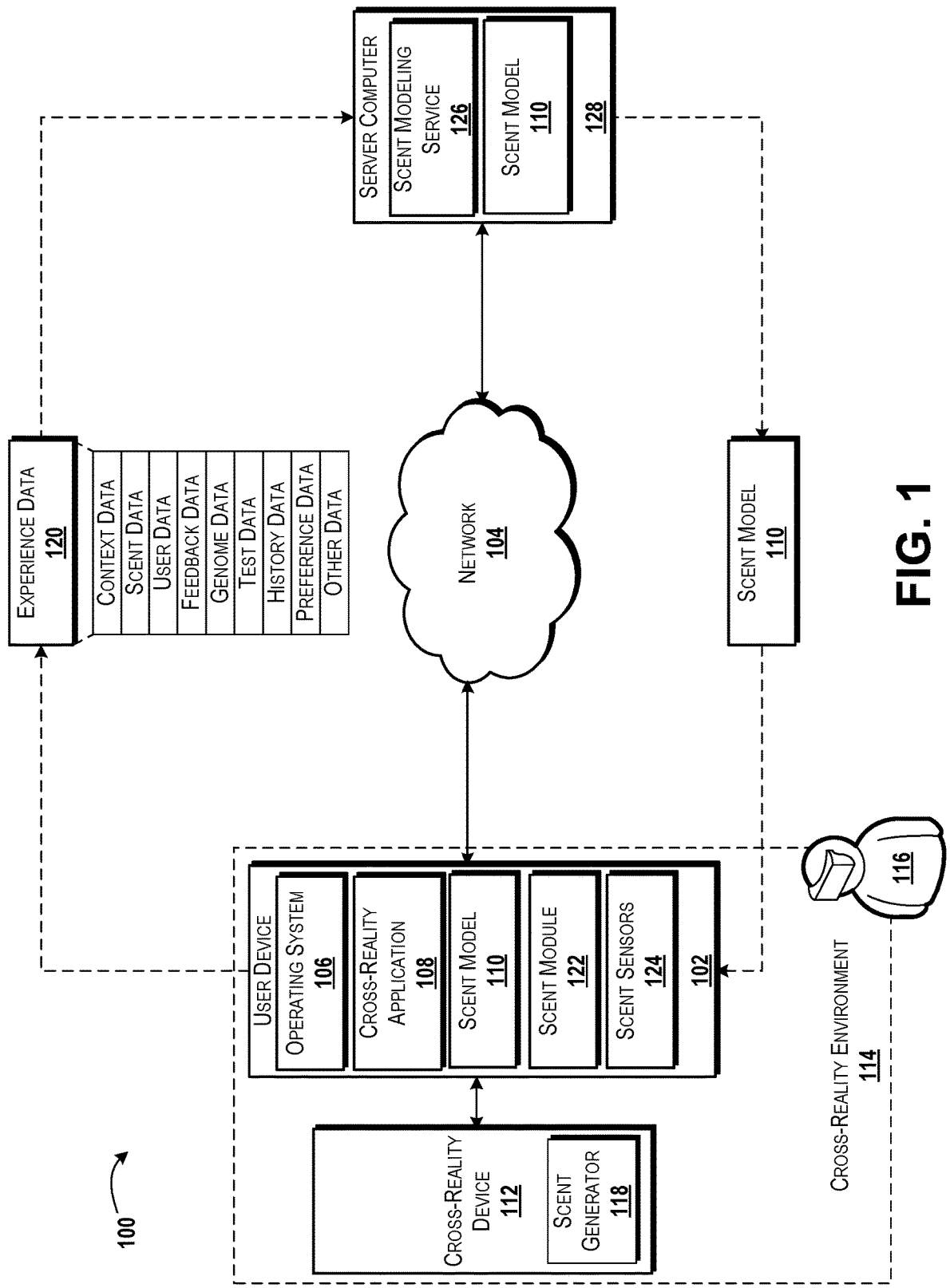
FIG. 1 is a system diagram illustrating an illustrative operating environment for various embodiments of the concepts and technologies described herein.

The following detailed description is directed to creating scent models and using scent models in cross-reality environments. A user device can be associated with a user. The user device can execute a scent module or the scent module can be included as part of a cross-reality application. The scent module can be configured to capture one or more scents (e.g., using the scent sensors) at various times, as well as various other information associated with the scent experience such as a geographic location at which the scent experience occurred, context associated with the scent experience (e.g., what the user and/or user device were doing when the scent experience occurred), user data that identifies the user and/or user device, history and/or preferences associated with the scents detected by the user device, combinations thereof, or the like. These and/or other information can be captured by the user device and provided to the scent modeling service for use in generating a scent model.

The scent modeling service can analyze one or more releases of the experience data to generate and/or update the scent model. The scent model can include a data structure that can define for a user, user device, cross-reality device, other entity and/or device, combinations thereof, or the like, various aspects of scents and/or smelling such as levels of sensitivity the user has for one or more scents, indication as to how long it takes a user to smell particular scents, preferences associated with the user for scents, contexts in which scents have been detected and/or indications as to how context may impact scent detection by the user, what scents should or should not be used, feedback relating to scent as obtained from the user, combinations thereof, or the like. The scent modeling service can store the scent model and/or can provide the scent model to the user device.

The cross-reality application can use the scent model to generate and/or optimize scent experiences in cross-reality sessions for the user. Thus, the cross-reality application can use the scent model to determine scents to emit using the scent generator, when to emit the scents using the scent generator, intensities of the scents to be emitted using the scent generator, timing (e.g., lead time, duration, linger time, etc.) of the scent emissions using the scent generator, combinations thereof, or the like. Thus, the scent model can be used to personalize the scent experience associated with the cross-reality device, thereby enhancing the use of scent in cross-reality sessions for the user. It should be understood that this example is illustrative, and therefore should not be construed as being limiting in any way.

While the subject matter described herein is presented in the general context of program modules that execute in conjunction with the execution of an operating system and application programs on a computer system, those skilled in the art will recognize that other implementations may be performed in combination with other types of program modules. Generally, program modules include routines, programs, components, data structures, and other types of structures that perform particular tasks or implement particular abstract data types. Moreover, those skilled in the art will appreciate that the subject matter described herein may be practiced with other computer system configurations, including hand-held devices, multiprocessor systems, microprocessor-based or programmable consumer electronics, minicomputers, mainframe computers, and the like.

Referring now to FIG. 1, aspects of an operating environment 100 for various embodiments of the concepts and technologies disclosed herein for creating scent models and using scent models in cross-reality environments will be described, according to an illustrative embodiment. The operating environment 100 shown in FIG. 1 includes a user device 102. The user device 102 can operate in communication with and/or as part of a communications network ("network") 104, though this is not necessarily the case.

According to various embodiments, the functionality of the user device 102 may be provided by one or more server computers, desktop computers, mobile telephones, laptop computers, set-top boxes, other computing systems, and the like. It should be understood that the functionality of the user device 102 may be provided by a single device, by two or more similar devices, and/or by two or more dissimilar devices. For purposes of describing the concepts and technologies disclosed herein, the user device 102 is described herein as a smartphone. It should be understood that this embodiment is illustrative, and therefore should not be construed as being limiting in any way.

The user device 102 can execute an operating system 106 and one or more application programs such as, for example, a cross-reality application 108. The operating system 106 can include a computer program that can control the operation of the user device 102. The cross-reality application 108 can include an executable program that can be configured to execute on top of the operating system 106 to provide various functions as illustrated and described herein for creating scent models and using scent models in cross-reality environments.

In particular, the cross-reality application 108 can be configured to provide a cross-reality session. As will be explained in more detail hereinbelow, the cross-reality application 108 can be configured to create a cross-reality session that includes the emission of scent using a scent model 110 that is personalized to an entity involved in the cross-reality session. The cross-reality session created by the cross-reality application 108 can be passed to a cross-reality device 112, which in turn can create the cross-reality environment 114 for the entity. For purposes of illustrating embodiments of the concepts and technologies disclosed herein, the entity involved in the cross-reality session will be illustrated and described herein as a user 116. It should be understood that this example is illustrative, and therefore should not be construed as being limiting in any way.

The cross-reality application 108 can generate the cross-reality session (e.g., creating rendering data for a rendered scene, processing audio, processing scent, other functions, combinations thereof, or the like) and pass cross-reality session data (not illustrated separately in FIG. 1) to the cross-reality device 112. The cross-reality device 112 can include, for example, one or more displays and/or connections to a display (e.g., a wireless or wired connection to a display and/or audio devices located on or at the user 116), one or more scent generators 118, audio devices, tactile output generators (e.g., treadmills, vibration machines, water sprayers, moving platforms, fans, lighting units, combinations thereof, or the like), and/or other hardware and/or software. Because the cross-reality device 112 can include additional and/or alternative components, it should be understood that this example is illustrative, and therefore should not be construed as being limiting in any way.

The scent generator 118 can include one or more scent banks, which can include one or more scent oils or the like.

The scent generator 118 also can include one or more scent emitters (e.g., an atomizing sprayer, or the like) and/or other hardware for generating scents. As will be explained in more detail herein, the cross-reality application 108 illustrated and described herein can include a scent module 122. The scent module 122 can include one or more module, application, program, process, other executable code, combinations thereof, or the like for generating a scent model 110 and/or for interacting with other entities and/or services to generate a scent model 110. It should be understood that although the functionality associated with the scent module is illustrated and described herein as being incorporated into the cross-reality application 108, that various embodiments of the concepts and technologies disclosed herein can include a separate module, application, or the like. As such, it should be understood that the illustrated example of the cross-reality application 108 is illustrative and should not be construed as being limiting in any way.

The scent module 122 (independently and/or as incorporated into the cross-reality application 108 and/or functioning independently) can be configured to track scent experiences associated with the user device 102 at a variety of times, including when involved in a cross-reality session and/or at other times, and to use this information to generate (or trigger generation of) a scent model 110. According to various embodiments of the concepts and technologies disclosed herein, the user device 102 can include one or more scent sensors 124, which can be configured to capture scent information (e.g., chemical compounds and/or scents detected at the user device 102, intensity of the detected scents (e.g., parts per million ("PPM") at which the scents are detected in the air, or the like). It should be understood that the scent model 110 can be generated at one time and used at a second time. As such, it can be appreciated that the user device 102 may not include the scent module 122 and/or the scent sensors 124 in some embodiments. It should be understood that this example is illustrative, and therefore should not be construed as being limiting in any way.

The scent module 122 can capture, along with the detected scents (e.g., captured by the scent sensors 124), various types of information associated with the scent experiences, and to create experience data 120 that relates to scents. According to various embodiments of the concepts and technologies disclosed herein, the experience data 120 can include context data, scent data, user data, feedback data, genome data, test data, history data, preference data, other data, or the like. These and/or other data can be captured by the user device 102 (e.g., via the scent module 122, the cross-reality application 108, and/or other entities), and used to create the scent model 110, as will be explained in more detail herein.

The context data can define a context detected when a scent experience occurs such as an activity in which the user 116 and/or user device 102 is involved in when the scent experience occurs, environmental conditions at the user device 102 when the scent experience occurs (e.g., temperature, noise levels, light levels, movements, other users present, etc.), one or more applications or processes being performed by the user device 102 when the scent experience occurs, and/or other context existing when the scent experience occurs. Thus, the context data can be used to determine what was occurring when the scent experience occurred. It should be understood that this example is illustrative, and therefore should not be construed as being limiting in any way.

The scent data can define contours of a scent detected when a scent experience occurs. Thus, the scent data can define, for example, scents detected, the intensity of the scent (e.g., parts per million ("PPM") of the scent in the tested air, perceived strength, etc.), the duration of the detection of the scent, and the like. Thus, the scent data can be used to identify the scent, the intensity of the scent, the perceived intensity of the scent, and/or the duration of the scent associated with a scent experience. Thus, the scent data can be used to determine what was smelled and for how long when the scent experience occurred. It should be understood that this example is illustrative, and therefore should not be construed as being limiting in any way.

The user data can define a user associated with a scent experience. Thus, the user data can identify the user device 102 and/or the user 116. According to various embodiments of the concepts and technologies disclosed herein, the user data can include biometric information (e.g., fingerprints, facial characteristics, or the like), authentication information (e.g., login and password information, or the like), device identifiers (e.g., international mobile subscriber identity ("IMSI") information, international mobile equipment identifier ("MEI") information, multimedia access control ("MAC") address information, IP address information, or the like), user name, other identifiers, or the like. Thus, the user data can be used to determine what user or device was involved in the scent experience. It should be understood that this example is illustrative, and therefore should not be construed as being limiting in any way.

The feedback data can define a context detected when a scent experience occurs such as an activity in which the user 116 and/or user device 102 is involved in when the scent experience occurs, environmental conditions at the user device 102 when the scent experience occurs (e.g., temperature, noise levels, light levels, movements, other users present, etc.), one or more applications or processes being performed by the user device 102 when the scent experience occurs, and/or other context existing when the scent experience occurs. Thus, the context data can be used to determine what was occurring when the scent experience occurred. It should be understood that this example is illustrative, and therefore should not be construed as being limiting in any way.

The genome data can define genetic and/or genome characteristics associated with the user 116 involved with a scent experience. The genome data can be obtained, for example, from a genealogy website (e.g., login information for a genealogy website, social network information, or the like) or other source that can be used to determine a genetic background associated with the user 116. This information can be used to determine relative strength of the scent perception of the user 116, in some embodiments. It should be understood that this example is illustrative, and therefore should not be construed as being limiting in any way.

The test data can define test results for the user 116 during a scent test. As will be explained in more detail herein, a scent test can be used to determine how a user 116 perceives scent (e.g., what scents, the intensity of those scents, etc.) and this information can be provided as the test data. Thus, the test data can be used to determine how scents are perceived by the user 116, the intensity of perceived scents by the user 116, combinations thereof, or the like. Thus, the test data can be used to determine the absolute and/or relative strength of the sense of smell of the user 116. In various embodiments of the concepts and technologies disclosed herein, the scent test illustrated and described herein can be provide by the user device 102 using the scent generator 118.

In some embodiments, the scent generator 118 can be used to present various scents and to measure reactions and/or feedback. Furthermore, the scent sensors 124 can be used during the scent test to measure intensities (e.g., PPM of the scent in the air) of the scents during the scent test, and user feedback can be obtained regarding intensity as well. Thus, it can be appreciated that the test data can define, for each scent, an objective measure of intensity (e.g., PPM in the air) and a subjective measure of intensity (e.g., a user indication of perceived intensity). It should be understood that this example is illustrative, and therefore should not be construed as being limiting in any way.

The history data can define one or more history associated with scent experiences in which the user 116 and/or user device 102 are involved. Thus, the history data can define how scents historically have been smelled, as well as when, where, and in what context the scent experiences have occurred. Thus, the history data can be used to determine trends and/or histories of scent experiences for the user 116 and/or user device 102. It should be understood that this example is illustrative, and therefore should not be construed as being limiting in any way.

The preference data can define one or more preferences for the user 116 and/or user device 102 relating to scents. For example, the preferences can define what scents the user 116 likes, what scents the user 116 does not like, combinations of scents that the user 116 likes or does not like, combinations thereof, or the like. Thus, the preference data can be used to determine likes and dislikes of the user 116 with regard to scents and/or scent experiences. It should be understood that this example is illustrative, and therefore should not be construed as being limiting in any way.

The other data can include various other information associated with scents such as distance of the user 116 from the object emitting scents during the scent experiences, geographic locations of the scent experiences (e.g., determined with a GPS receiver of the user device 102 or cross-reality device 112), other users in proximity to the user 116, or other information. The other data can also include any other information as illustrated and described herein. It should be understood that this example is illustrative, and therefore should not be construed as being limiting in any way.

The experience data 120 can be created at the user device 102 (e.g., via the scent module 122, the cross-reality application 108, and/or other functionality) and provided to a scent modeling service 126 or other application or service, which can be hosted and/or executed by a device such as the server computer 128 illustrated in FIG. 1. The scent modeling service 126 can be configured to generate, store, update, and/or provide one or more scent models 110 to one or more devices such as the user device 102. According to various embodiments of the concepts and technologies disclosed herein, the scent modeling service 126 can be configured to obtain the experience data 120, analyze the experience data 120, and generate the scent model 110 based on the analysis. In various embodiments, the user perception can be coupled with user biometrics and genome data to determine the emotive response (and feedback) for individual users 116 and scents at various intensities. Specifically, using various attributes of the experience data 120, the system may evaluate a scent model 110 in a context that is endearing (e.g., a positive family or work experience) and in a context that is discomforting (e.g., a synthesized monster or high-stress experience) and add the feedback to the overall experience data 120. It should be understood that this example is illustrative, and therefore should not be construed as being limiting in any way.

According to various embodiments of the concepts and technologies disclosed herein, the analysis of the experience data 120 can be performed to determine how a user 116 (or other entity associated with the user device 102 and/or the cross-reality device 112) perceives scents, and this information can be used to personalize a scent experience associated with a cross-reality session, as explained herein. Thus, the scent modeling service 126 can be configured to analyze a first received instance or release of the experience data 120 to create the scent model 110 and subsequent instances or releases of the experience data 120 to update the scent model 110. It should be understood that this example is illustrative, and therefore should not be construed as being limiting in any way.

When creating the scent model 110, the scent modeling service 126 can determine, for one or more contexts (e.g., activities in which the user 116 and/or the user device 102 have been engaged in during a scent experience) during which scent was perceived, what scents were detected, how strong the perception was, any user feedback relating to the scent (e.g., the user 116 liked the scent, did not like the scent, easily smelled the scent, did not easily smell the scent, a mood associated with the scent, etc.), history data (e.g., times at which this scent has been perceived and/or historical responses to the scent by the user 116), preference data (e.g., likes and/or dislikes and the like), and/or other information.

These and/or other data can be used to generate the scent model 110, which can relate, for each context and/or scent, how a user 116 or other entity associated with the user device 102 perceives that scent and/or can be expected to react to that scent, for example, timing of scent perceptions, strength of response to the scents, etc. These and/or other reactions of the user 116 to scent can be recorded in the scent model 110 so that scent experiences in cross-reality sessions can be personalized to the user 116 or other entity associated with the user device 102.

The scent modeling service 126 also can be configured to use test data (e.g., data obtained by the user device 102 during a scent test administered to the user 116 or other user associated with the user device 102) that can be used to determine similar scent perception information for the user 116. Also, the scent modeling service 126 can be configured to access and/or obtain genome data (e.g., obtain genetic relationships via genealogy web sites or the like) to determine genetic assumptions regarding scent perception for the user 116 based on relationships and/or known information associated with genealogy of the user 116. Because the particulars of the scent model 110 can be determined in various manners as illustrated and described herein, it should be understood that these examples are illustrative, and therefore should not be construed as being limiting in any way.

Upon generating a scent model 110 for a user 116 (or other entity associated with the user device 102), the scent modeling service 126 can store the scent model 110 locally (e.g., at the server computer 128) and/or remotely (e.g., at a data server, database, or the like), if desired. In various embodiments, the server computer 128 can be configured to provide the scent model 110 to the user device 102 and/or the cross-reality device 112, and the scent model 110 can be used in cross-reality sessions. The scent modeling service 126 can be configured to update the scent model 110 at various times using one or more instances or releases of the experience data 120.

According to various embodiments of the concepts and technologies disclosed herein, the cross-reality application 108 can generate one or more scents and/or combinations of scents for a cross-reality session. Thus, for example, if a user 116 involved in a cross-reality session is shown a scene involving walking into a restaurant, for example, the cross-reality device 112 (or a scent generator thereof) can be configured to generate one or more scents and/or combinations thereof that are appropriate for a restaurant environment (e.g., a scent of coffee, a scent of doughnuts, etc.). Thus, an added level of realism can be introduced to the cross-reality session. According to various embodiments of the concepts and technologies disclosed herein, the cross-reality application 108 can use a scent model 110 for generating the scents in the cross-reality session, where the scent model 110 can inform the cross-reality device 112 the amounts of scents to emit, scents to use and/or not to use, the timing of the emission of the scents, and the like; all as determined appropriate (according to the scent model 110) for the user 116 involved in the cross-reality session. It should be understood that this example is illustrative, and therefore should not be construed as being limiting in any way.

In an example embodiment of the concepts and technologies disclosed herein, the scent model 110 can include a data structure that can define, for a user 116, user device 102, cross-reality device 112, other entity and/or device, combinations thereof, or the like, various aspects of scents and/or smelling. Thus, for example, an example embodiment of the concepts and technologies disclosed herein includes a data structure (e.g., a table, database, or the like) that can include, for each scent in a scent generator bank (e.g., all scents available for a scent generator of the cross-reality device 112), a level of sensitivity the user 116 has for that scent; an indication as to timing of the scent in cross-reality sessions (e.g., a lead time the scent should be emitted before the item "appears" in the cross-reality scene and/or a duration of the scent emission after the item has "exited" the cross-reality scene), scents that should or should not be used, combinations thereof, or the like. It can be appreciated that these and/or other parameters included in the scent model 110 can be based on feedback and/or testing data obtained from the user 116 during one or more real world and/or cross-reality session experiences (e.g., in the experience data 120 as illustrated and described herein). Thus, once a scent model 110 is created for a user 116, that scent model 110 can be used to personalize the scent experience associated with the cross-reality session for the user 116. It should be understood that this example is illustrative, and therefore should not be construed as being limiting in any way.

In practice, a user device 102 can be associated with a user 116. The user device 102 can execute a scent module 122 or the scent module 122 can be included as part of a cross-reality application 108. The scent module 122 can be configured to capture one or more scents (e.g., using the scent sensors 124) at various times, as well as various other information associated with the scent experience such as a geographic location at which the scent experience occurred, context associated with the scent experience (e.g., what the user 116 and/or user device 102 were doing when the scent experience occurred), user data that identifies the user 116 and/or user device 102, history and/or preferences associated with the scents detected by the user device 102, combinations thereof, or the like. These and/or other information can be captured by the user device 102 and provided to the scent modeling service 126 for use in generating a scent model 110.

The scent modeling service 126 can analyze one or more releases of the experience data 120 to generate and/or update the scent model 110. The scent model 110 can include a data structure that can define for a user 116, user device 102, cross-reality device 112, other entity and/or device, combinations thereof, or the like, various aspects of scents and/or smelling such as levels of sensitivity the user 116 has for one or more scents, indication as to how long it takes a user 116 to smell particular scents, preferences associated with the user for scents, contexts in which scents have been detected and/or indications as to how context may impact scent detection by the user 116, what scents should or should not be used, feedback relating to scent as obtained from the user 116, combinations thereof, or the like. The scent modeling service 126 can store the scent model 110 and/or can provide the scent model 110 to the user device 102.

The cross-reality application 108 can use the scent model 110 to generate and/or optimize scent experiences in cross-reality sessions for the user 116. Thus, the cross-reality application 108 can use the scent model 110 to determine scents to emit using the scent generator 118, when to emit the scents using the scent generator 118, intensities of the scents to be emitted using the scent generator 118, timing (e.g., lead time, duration, linger time, etc.) of the scent emissions using the scent generator 118, combinations thereof, or the like. Thus, the scent model 110 can be used to personalize the scent experience associated with the cross-reality device 112, thereby enhancing the use of scent in cross-reality sessions for the user 116. It should be understood that this example is illustrative, and therefore should not be construed as being limiting in any way.

FIG. 1 illustrates one user device 102, one network 104, one cross-reality device 112, and one server computer 128. It should be understood, however, that various implementations of the operating environment 100 can include one or more than one user device 102; one or more than one cross-reality device 112; and/or zero, one, or more than one server computer 128. As such, the illustrated embodiment should be understood as being illustrative, and should not be construed as being limiting in any way.

Figure 2:
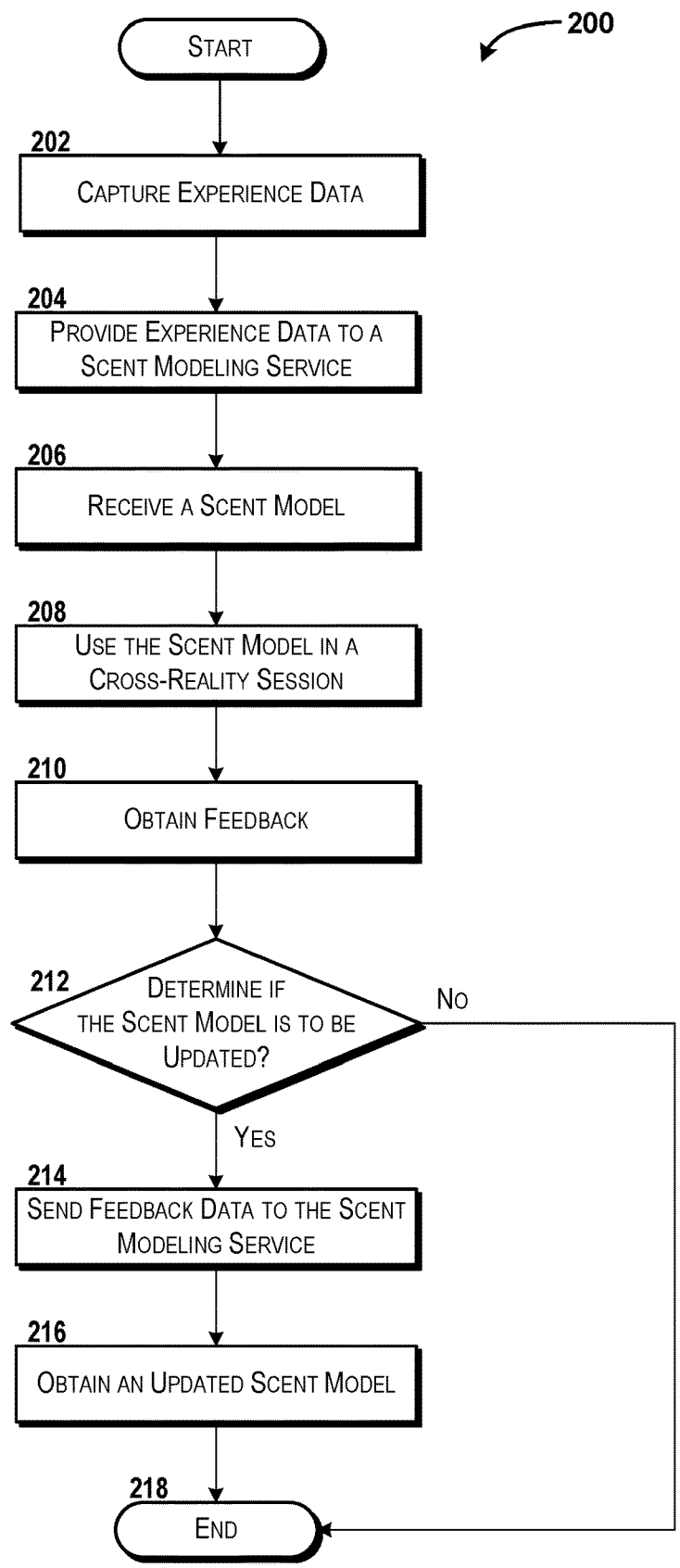
FIG. 2 is a flow diagram showing aspects of a method for creating scent models and using scent models in cross-reality environments, according to an illustrative embodiment of the concepts and technologies described herein.

Turning now to FIG. 2, aspects of a method 200 for creating scent models and using scent models in cross-reality environments will be described in detail, according to an illustrative embodiment. It should be understood that the operations of the methods disclosed herein are not necessarily presented in any particular order and that performance of some or all of the operations in an alternative order(s) is possible and is contemplated. The operations have been presented in the demonstrated order for ease of description and illustration. Operations may be added, omitted, and/or performed simultaneously, without departing from the scope of the concepts and technologies disclosed herein.

It also should be understood that the methods disclosed herein can be ended at any time and need not be performed in its entirety. Some or all operations of the methods, and/or substantially equivalent operations, can be performed by execution of computer-readable instructions included on a computer storage media, as defined herein. The term "computer-readable instructions," and variants thereof, as used herein, is used expansively to include routines, applications, application modules, program modules, programs, components, data structures, algorithms, and the like. Computer-readable instructions can be implemented on various system configurations including single-processor or multiprocessor systems, minicomputers, mainframe computers, personal computers, hand-held computing devices, microprocessor-based, programmable consumer electronics, combinations thereof, and the like.

Thus, it should be appreciated that the logical operations described herein are implemented (1) as a sequence of computer implemented acts or program modules running on a computing system and/or (2) as interconnected machine logic circuits or circuit modules within the computing system. The implementation is a matter of choice dependent on the performance and other requirements of the computing system. Accordingly, the logical operations described herein are referred to variously as states, operations, structural devices, acts, or modules. These states, operations, structural devices, acts, and modules may be implemented in software, in firmware, in special purpose digital logic, and any combination thereof. As used herein, the phrase "cause a processor to perform operations" and variants thereof is used to refer to causing a processor of a computing system or device, such as the user device 102 and/or the server computer 128, to perform one or more operations and/or causing the processor to direct other components of the computing system or device to perform one or more of the operations.

For purposes of illustrating and describing the concepts of the present disclosure, the method 200 is described herein as being performed by the user device 102 via execution of one or more software modules such as, for example, the cross-reality application 108. It should be understood that additional and/or alternative devices and/or network nodes can provide the functionality described herein via execution of one or more modules, applications, and/or other software including, but not limited to, the cross-reality application 108. Thus, the illustrated embodiments are illustrative, and should not be viewed as being limiting in any way.

The method 200 begins at operation 202. At operation 202, the user device 102 can capture experience data 120. In various embodiments of the concepts and technologies disclosed herein, as noted above, the cross-reality application 108 can include a scent module to capture and/or create the experience data 120. As explained above, the experience data 120 can include context data that can describe, for example, an activity and/or action associated with the user device 102 and/or the user 116, ambient conditions around the user device 102 (e.g., in proximity to the user device 102 and/or the cross-reality device 112), movements of the user 116 and/or user device 102, combinations thereof, or the like. Thus, operation 202 can correspond to the user device 102 capturing, directly, via sensors, via the cross-reality device 112, and/or other devices, the context data illustrated and described herein. It should be understood that this example is illustrative, and therefore should not be construed as being limiting in any way.

As explained herein, the experience data 120 captured at operation 202 also can include scent data. The scent data can describe, for example, a scent in an environment that is in proximity to the user 116 (e.g., as sensed through one or more scent sensors located at the user device 102 and/or the cross-reality device 112), a scent indicated by a user 116 (e.g., via one or more interfaces presented to the user 116), and/or other scents that are detected at or in proximity to the user device 102 and/or the cross-reality device 112. Thus, operation 202 can correspond to the user device 102 and/or the cross-reality device 112 capturing via one or more scent sensors, the scent data illustrated and described herein. It should be understood that this example is illustrative, and therefore should not be construed as being limiting in any way.

The experience data 120 captured in operation 202 also can include user data, as explained above. The user data can identify the user 116. In some embodiments, the user data can identify the user 116 while in some other embodiments the user data can identify the user device 102 and/or the cross-reality device 112. The user data can be used to associate the experience data 120 with the user 116. Thus, operation 202 can correspond to the user device 102 and/or the cross-reality device 112 capturing the user data illustrated and described herein. It should be understood that this example is illustrative, and therefore should not be construed as being limiting in any way.

The experience data 120 also can include test data. The test data can describe, for example, input captured during a test performed by a user 116 (e.g., a scent test) to determine strength/accuracy of the sense of smell of the user 116. Thus, for example, the experience data 120 can capture information that describes what scents a user 116 smells and how those scents are determined by the scent sensors of the user device 102 and/or the cross-reality device 112. Thus, it can be appreciated that the experience data 120 also can include feedback data such as feedback provided by the user 116 during testing and/or the like. Thus, operation 202 can correspond to the user device 102 and/or the cross-reality device 112 capturing the test data and/or feedback data illustrated and described herein. It should be understood that this example is illustrative, and therefore should not be construed as being limiting in any way.

These and other types of experience data 120 can be captured in operation 202 and formatted into a data file or data stream that can be provided by the user device 102 to the server computer 128 (e.g., to the scent modeling service 126 hosted and/or executed thereby). In various embodiments, the experience data 120 can be captured at various times (e.g., at time intervals, when changes in scents are detected, when requested or triggered, other times, combinations thereof, or the like). Because the experience data 120 can be captured at additional and/or alternative times, it should be understood that these examples are illustrative, and therefore should not be construed as being limiting in any way.

From operation 202, the method 200 can proceed to operation 204. At operation 204, the user device 102 can provide the experience data 120 captured in operation 202 to the scent modeling service 126. According to various embodiments of the concepts and technologies disclosed herein, the server computer 128 can expose a portal, an application programming interface ("API"), or other functionality via which the experience data 120 can be provided to the server computer 128. In some other embodiments, the user device 102 can send (or trigger sending of) the experience data 120 to the server computer 128 via the network 104 using a data transfer or the like. In yet other embodiments, the user device 102 can stream the experience data 120 and/or release or publish the experience data 120 at various times as noted above. Because the user device 102 can provide the experience data 120 to the server computer 128 in additional and/or alternative manners, it should be understood that these examples are illustrative, and therefore should not be construed as being limiting in any way.

From operation 204, the method 200 can proceed to operation 206. At operation 206, the user device 102 can receive a scent model 110. According to various embodiments of the concepts and technologies disclosed herein, the user device 102 can obtain a scent model 110 that relates to the user 116 and/or the user device 102 from the server computer 128 and/or the scent modeling service 126 hosted and/or executed thereby. In additional embodiments, the scent modeling service 126 may have a multitude of scent models 110 that are determined to be best matches according to the user device 102, the cross-reality device 112, or recent (profile archived) experience data 120. The best match determination may use any of these attributes that may be optimized dynamically by the immediate experience or pre-determined by prior rules governing the cross-reality environment 114, the user 116, or the network 104. It therefore can be appreciated that in some embodiments of the method 200, operations 202-204 can correspond to the operations of the user device 102 for creating the scent model 110, though this is not necessarily the case. In operation 206, the user device 102 can receive the scent model 110, which can be based on the experience data 120 and therefore can be used to provide scents to the user 116 and/or user device 102 as explained herein. It should be understood that this example is illustrative, and therefore should not be construed as being limiting in any way.

From operation 206, the method 200 can proceed to operation 208. At operation 208, the user device 102 can use the scent model 110 in a cross-reality session. As explained herein, the scent model 110 can be used to provide personalized scents to a user 116 during one or more cross-reality sessions (and/or virtual reality or augmented reality sessions). The scent model 110 can represent, to the cross-reality application 108 that uses the scent model 110 to provide scent during the cross-reality session, various abilities, preferences, and/or the like for the user 116. Thus, operation 208 can correspond to the user device 102 modifying (e.g., via the cross-reality application 108 and/or via the cross-reality device 112) an intensity of the scents provided to the user 116, modifications to certain scents (e.g., a scent model 110 for a user 116 may indicate that the user 116 mistakes lemon scent for lime scent unless the lemon scent is doubled relative to what most users receive by way of example), timing of the scents provided to the user 116, scents the user 116 does and/or does not like, combinations thereof, or the like.

Thus, operation 208 can correspond to the user device 102 customizing and/or personalizing the scent experience for the user 116 in the cross-reality session based on the scent model 110, which itself can be based on experience data 120 captured from previous interactions of the user 116 with scents. Because these and/or other adjustments to the scent experience of the user 116 in the cross-reality session can be made in accordance with the concepts and technologies disclosed herein, it should be understood that these examples are illustrative, and therefore should not be construed as being limiting in any way.

From operation 208, the method 200 can proceed to operation 210. At operation 210, the user device 102 can obtain feedback. According to various embodiments of the concepts and technologies disclosed herein, the user device 102 can obtain feedback from the user 116 via one or more user interfaces. The user interfaces can ask a user 116 for feedback regarding scents provided during a cross-reality session. The feedback can indicate if one or more scents were accurate (e.g., an indication as to whether the scents smelled like the scents that were supposed to be provided to the user 116 during the cross-reality session, an indication as to whether the user 116 identified the intensity of the scents as being correct (e.g., not too weak, not too strong, etc.), that the scent was timed correctly in the cross-reality session (e.g., the scent was perceived by the user 116 at the time expected in the cross-reality session), combinations thereof, or the like). According to various embodiments of the concepts and technologies disclosed herein, the user device 102 can present one or more user interfaces to obtain the feedback in operation 210. It should be understood that this example is illustrative, and therefore should not be construed as being limiting in any way.

From operation 210, the method 200 can proceed to operation 212. At operation 212, the user device 102 can determine if the scent model 110 is to be updated. In various embodiments of the concepts and technologies disclosed herein, the determination of operation 212 can be based on the feedback obtained in operation 210. Additionally, or alternatively, it can be appreciated that the scent model 110 can be updated based on history of the user 116 and/or the user device 102, and therefore the determination of operation 212 can correspond to determining that a scent has been presented to the user 116 in a cross-reality session and therefore the scent model 110 should be updated. Because the user device 102 can determine that the scent model 110 should be updated in additional and/or alternative manners, it should be understood that these examples are illustrative, and therefore should not be construed as being limiting in any way.

If the user device 102 determines, in operation 212, that the scent model 110 is to be updated, the method 200 can proceed to operation 214. At operation 214, the user device 102 can send feedback data to the scent modeling service 126. In some embodiments, the feedback data can be provided by the user device 102 to the server computer 128 and/or the scent modeling service 126 as or in a next release of the experience data 120, though this is not necessarily the case. It should be understood that this example is illustrative, and therefore should not be construed as being limiting in any way.

From operation 214, the method 200 can proceed to operation 216. At operation 216, the user device 102 can obtain an updated scent model 110. It can be appreciated that operation 216 can correspond to the server computer 128 (e.g., via execution of the scent modeling service 126) sending an updated scent model 110 to the user device 102. In some embodiments, the server computer 128 can generate the updated scent model 110. The server computer 128 can store the updated scent model 110 as well, in some embodiments. It should be understood that this example is illustrative, and therefore should not be construed as being limiting in any way.

From operation 216, the method 200 can proceed to operation 218. The method 200 also can proceed to operation 218 if the user device determines, in operation 212, that the scent model 110 is not to be updated. The method 200 can end at operation 218.

Figure 3:
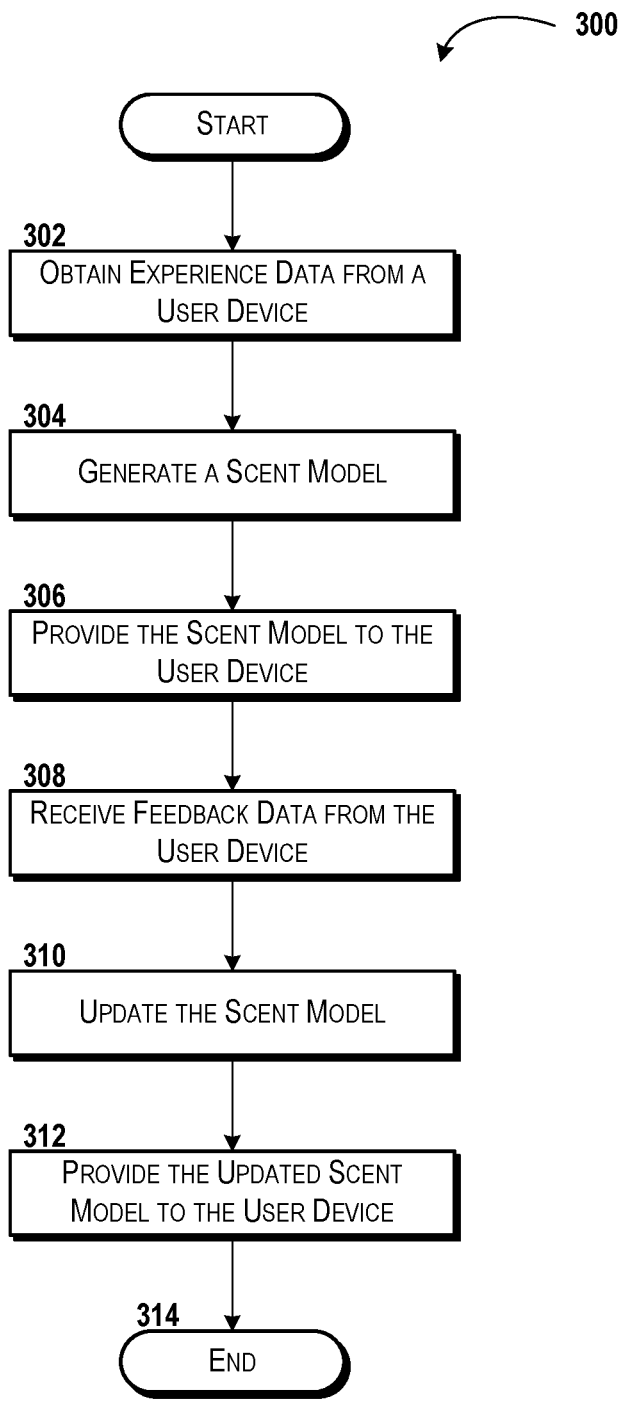
FIG. 3 is a flow diagram showing aspects of a method for creating scent models for use in cross-reality environments, according to an illustrative embodiment of the concepts and technologies described herein.

Turning now to FIG. 3, aspects of a method 300 for creating scent models for use in cross-reality environments will be described in detail, according to an illustrative embodiment. For purposes of illustrating and describing the concepts of the present disclosure, the method 300 is described herein as being performed by the server computer 128 via execution of one or more software modules such as, for example, the scent modeling service 126. It should be understood that additional and/or alternative devices and/or network nodes can provide the functionality described herein via execution of one or more modules, applications, and/or other software including, but not limited to, the scent modeling service 126. Thus, the illustrated embodiments are illustrative, and should not be viewed as being limiting in any way.

The method 300 begins at operation 302. At operation 302, the server computer 128 can obtain experience data 120 from the user device 102. According to various embodiments of the concepts and technologies disclosed herein, the experience data 120 can be streamed to the server computer 128 and/or released more than once (e.g., at time intervals, at trigger events such as use of a scent model 110 by the user device 102, and/or at other times). In various embodiments of the concepts and technologies disclosed herein, it can be appreciated that the performance of operation 302 by the server computer 128 can be performed in response to receiving experience data 120 provided by the user device 102 via execution of the operation 204 of the method 200. It should be understood that this example is illustrative, and therefore should not be construed as being limiting in any way.

From operation 302, the method 300 can proceed to operation 304. At operation 304, the server computer 128 can generate, based on the experience data 120 and/or other information, the scent model 110. It can be appreciated that the performance of operation 304 can correspond to the creation of a scent model 110 or an update of the scent model 110. Thus, it can be appreciated that the performance of operations 302-304 can correspond to creating or updating the scent model 110. The scent model 110 can describe various aspects of the user 116 with regard to scent such as, for example, an ability to smell scents (e.g., how much of a particular scent is required for the user 116 to smell the scent), an intensity required for the scent for the user 116 to perceive the scent, timing of the scent release in a cross-reality session to match a scene, etc. Thus, the scent model 110 can instruct the cross-reality device 112 how to provide scents to the user 116 in a cross-reality session where the scents are tailored and/or optimized for the user 116. It should be understood that this example is illustrative, and therefore should not be construed as being limiting in any way.

From operation 304, the method 300 can proceed to operation 306. At operation 306, the server computer 128 can provide the scent model 110 to the user device 102. According to various embodiments of the concepts and technologies disclosed herein, the scent model 110 can be provided to the user device 102 as part of a setup and/or configuration operation associated with the cross-reality application 108 and/or the scent modeling service 126. In some other embodiments, the scent model 110 can be provided at other times (e.g., when the scent model 110 is generated). Because the scent model 110 can be provided to the user device 102 at additional and/or alternative times, it should be understood that this example is illustrative, and therefore should not be construed as being limiting in any way.

From operation 306, the method 300 can proceed to operation 308. At operation 308, the server computer 128 can receive experience data 120 from the user device 102. According to various embodiments of the concepts and technologies disclosed herein, the experience data 120 can be obtained from the user device as a release or in a stream of experience data 120 as explained above. As noted above, the experience data 120 can include contextual information, scent information, history data, preferences, or the like. In various embodiments, the feedback data can indicate, for the user 116 associated with the user device 102 that provided the experience data 120, if one or more scents provided to the user 116 were accurate (e.g., an indication as to whether the scents smelled like the scents that were supposed to be provided to the user 116 during the cross-reality session, an indication as to whether the user 116 identified the intensity of the scents as being correct (e.g., not too weak, not too strong, etc.), that the scent was timed correctly in the cross-reality session (e.g., the scent was perceived by the user 116 at the time expected in the cross-reality session), combinations thereof, or the like). Because the experience data 120 can be obtained in additional and/or alternative times, it should be understood that this example is illustrative, and therefore should not be construed as being limiting in any way.

From operation 308, the method 300 can proceed to operation 310. At operation 310, the server computer 128 can update the scent model 110. It can be appreciated that the server computer 128 can update the scent model 110 based on the feedback data received in operation 308. Operation 310 can correspond to the server computer 128 updating the scent model 110 based on the preferences of the user 116, the history of the user 116, the feedback provided by the user 116, combinations thereof, or the like.

From operation 310, the method 300 can proceed to operation 312. At operation 312, the server computer 128 can provide the updated scent model 110 to the user device 102. According to various embodiments of the concepts and technologies disclosed herein, the updated scent model 110 can be provided to the user device 102 for use in future cross-reality sessions. Because the updated scent model 110 can be provided for additional and/or alternative reasons, it should be understood that this example is illustrative, and therefore should not be construed as being limiting in any way.

From operation 312, the method 300 can proceed to operation 314. The method 300 can end at operation 314.

Figure 4A:
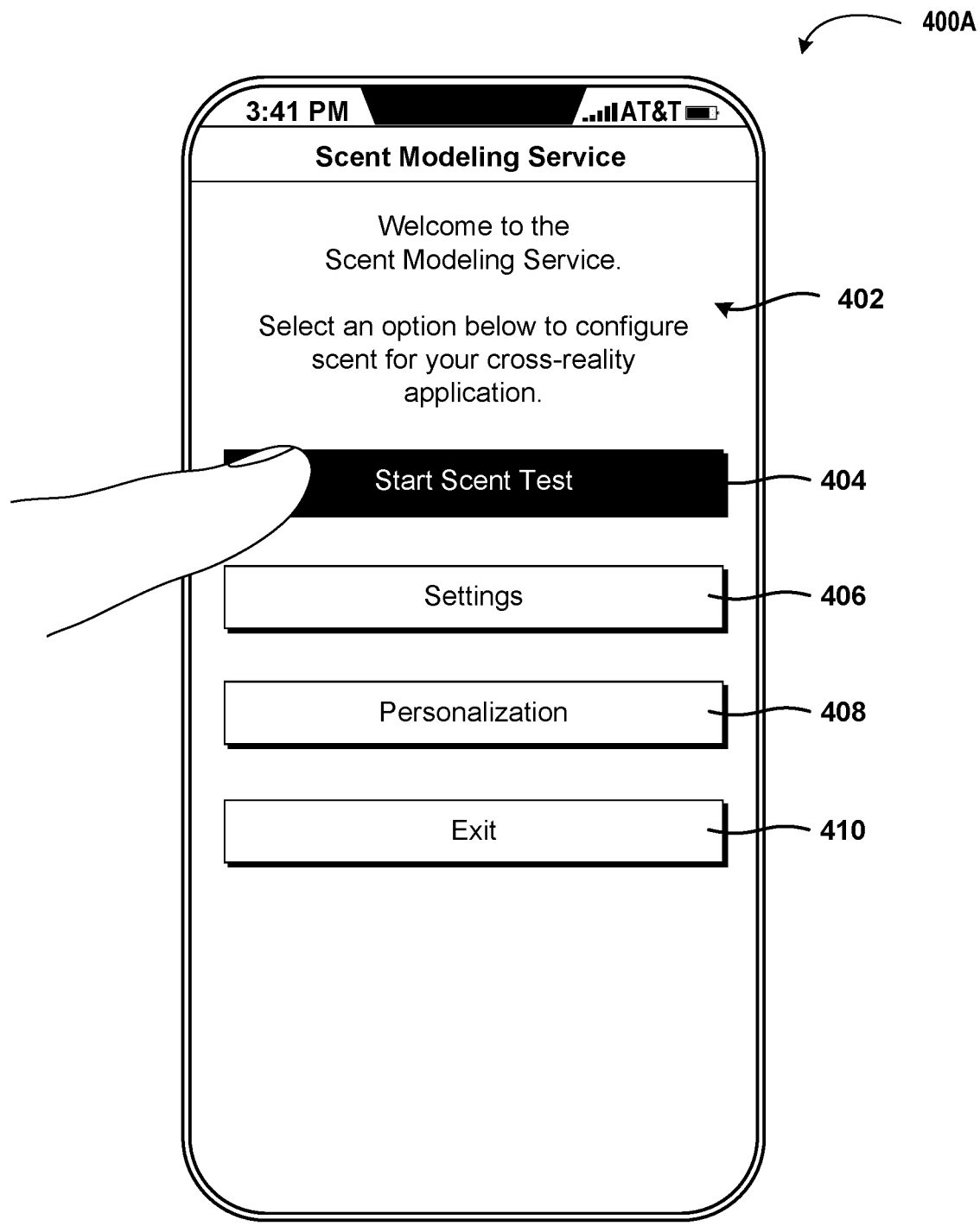
FIGS. 4A-4B are user interface diagrams showing various screen displays for creating scent models and using scent models in cross-reality environments, according to some illustrative embodiments of the concepts and technologies described herein.
Figure 4B:
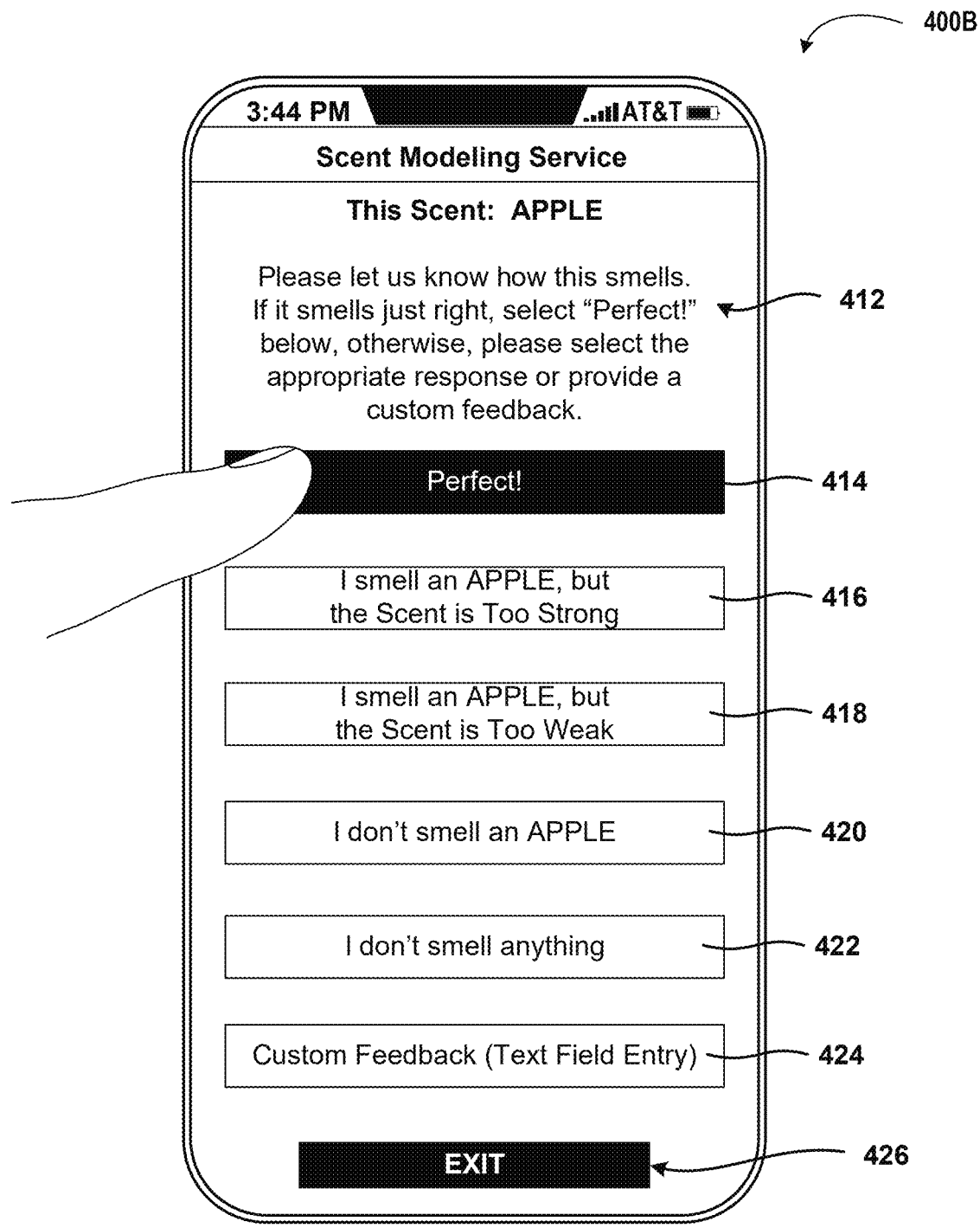

FIGS. 4A-4B are user interface ("UP") diagrams showing aspects of UIs for using and/or interacting with the cross-reality application 108 and/or the scent modeling service 126, according to some illustrative embodiments. FIG. 4A shows an illustrative screen display 400A. According to some embodiments of the concepts and technologies described herein, the screen display 400A can be generated by a device such as the user device 102 via interactions with the cross-reality application 108 and/or the scent modeling service 126. In particular, according to various embodiments, the user device 102 can generate the screen display 400A and/or other screen displays in conjunction with and/or based upon interactions with the cross-reality application 108 and/or the scent modeling service 126 described herein, which can be configured to render the screen display 400A using data generated at the user device 102 and/or using data provided by the scent modeling service 126. It should be appreciated that the UI diagram illustrated in FIG. 4A is illustrative of one contemplated example of the UIs that can be generated and/or displayed in accordance with the concepts and technologies disclosed herein, and therefore should not be construed as being limiting in any way.

According to various embodiments, the screen display 400A can be presented, for example, when a user 116 or other entity configures the cross-reality application 108 and/or the scent modeling service 126, when providing personalization for the cross-reality application 108 and/or the scent modeling service 126, when providing feedback to the cross-reality application 108 and/or the scent modeling service 126, or at other times. Because the screen display 400A illustrated in FIG. 4A can be displayed at additional and/or alternative times, it should be understood that these examples are illustrative and therefore should not be construed as being limiting in any way.

The screen display 400A can include various menus and/or menu options (not shown in FIG. 4A). The screen display 400A also can include a scent modeling service configuration screen 402. The scent modeling service configuration screen 402 can be configured to present various controls and/or options to enable a user 116 to interact with the cross-reality application 108 and/or the scent modeling service 126 to configure various aspects of creating and/or using scent models 110. It should be understood that this example is illustrative, and therefore should not be construed as being limiting in any way.

As shown in the illustrated embodiment, the scent modeling service configuration screen 402 can include a start scent test option 404. The start scent test option 404 can be selectable to launch a scent test and/or other operations for testing functionality associated with the cross-reality application 108 for using scent models 110. Thus, selection of the start scent test option 404 can cause the user device 102 and/or the cross-reality device 112 to begin presenting various scents and obtain feedback from the user 116 relating to the scents. An example user interface for providing the scent test to the user 116 will be illustrated and described hereinbelow with reference to FIG. 4B. At any rate, selection of the start scent test option 404 can cause the user device 102 to present additional and/or alternative information and/or controls. It should be understood that this example is illustrative and therefore should not be construed as being limiting in any way.

As shown in FIG. 4A, the scent modeling service configuration screen 402 also can include a configure settings option 406. Selection of the configure settings option 406 can cause the user device 102 to present various configuration options for the cross-reality application 108 and/or the scent modeling service 126 such as, for example, when scents should be collected, when scents should not be collected, when a scent model 110 should be used to generate and/or provide scents in cross-reality environments 114, when a scent model 110 should not be used to generate and/or provide scents in cross-reality environments 114, other options, combinations thereof, or the like. Thus, it can be appreciated that selection of the configure settings option 406 can cause the user device 102 to present various other screen displays and/or options for modifying and/or setting various options associated with the cross-reality application 108 and/or the scent modeling service 126. It should be understood that the illustrated configure settings option 406 is illustrative and therefore should not be construed as being limiting in any way.

The scent modeling service configuration screen 402 also can include a personalization option 408. Selection of the personalization option 408 can cause the user device 102 to present various personalization options for the cross-reality application 108 and/or the scent modeling service 126 such as, for example, what scents the user 116 likes, what scents the user 116 does not like, a relative strength and/or weakness of the sense of smell of the user 116, histories and/or scent test results associated with the user 116, genetic and/or genome information associated with the user 116, combinations thereof, or the like. Thus, it can be appreciated that selection of the personalization option 408 can cause the user device 102 to present various other screen displays and/or options for modifying and/or setting various personalization data and/or options associated with the cross-reality application 108 and/or the scent modeling service 126. It should be understood that the illustrated personalization option 408 is illustrative and therefore should not be construed as being limiting in any way.

The scent modeling service configuration screen 402 also can include a UI control 410 to dismiss the scent modeling service configuration screen 402. Thus, for example, the user or other entity can select the UI control 410 to cause the user device 102 to close the scent modeling service configuration screen 402 when the desired information has been obtained via the scent modeling service configuration screen 402, when the user or other entity wishes to close the scent modeling service configuration screen 402 for other reasons, and/or at other times at which the UI control 410 is selected. Because additional or alternative controls can be included in the scent modeling service configuration screen 402, it should be understood that the example embodiment shown in FIG. 4A is illustrative and therefore should not be construed as being limiting in any way.

FIG. 4B shows an illustrative screen display 400B. According to some embodiments of the concepts and technologies described herein, the screen display 400B can be generated by a device such as the user device 102 via interactions with the cross-reality application 108 and/or the scent modeling service 126. In particular, according to various embodiments, the user device 102 can generate the screen display 400B and/or other screen displays in conjunction with and/or based upon interactions with the cross-reality application 108 and/or the scent modeling service 126 to perform a scent test for a user 116. Because the screen display 400B illustrated in FIG. 4B can be displayed at additional and/or alternative times, it should be understood that this example is illustrative and therefore should not be construed as being limiting in any way. For example, this feedback may be additionally collected via voice responses or passively inferred from biometric and reactionary responses from the experience data 120.

The screen display 400B can include various menus and/or menu options (not shown in FIG. 4B). The screen display 400B also can include a scent test screen 412. The scent test screen 412 can be configured to present an indication of a scent being generated by the cross-reality device 112. In the illustrated embodiment, the scent test screen 412 indicates that an apple scent is being generated. The scent test screen 412 also includes one or more options for providing feedback regarding the scent being generated. It should be understood that this example is illustrative, and therefore should not be construed as being limiting in any way.

As shown in the illustrated embodiment, the scent test screen 412 can include a UI control 414 that can be selected to indicate that the scent being generated by the cross-reality device 112 (or other hardware) is accurate. The scent test screen 412 also can include a UI control 416 that can be selected to indicate that the scent being generated by the cross-reality device 112 (or other hardware) is accurate, but too strong (e.g., too intense, too easy to smell, overpowering, or the like). The scent test screen 412 also can include a UI control 418 that can be selected to indicate that the scent being generated by the cross-reality device 112 (or other hardware) is accurate, but too weak (e.g., not intense enough, difficult to smell, or the like). The scent test screen 412 also can include a UI control 420 that can be selected to indicate that the scent being generated by the cross-reality device 112 (or other hardware) is inaccurate (e.g., does not smell like the scent allegedly being generated, or the like). The scent test screen 412 also can include a UI control 422 that can be selected to indicate that the scent being generated by the cross-reality device 112 (or other hardware) is not detectable by the user (e.g., the user does not smell anything allegedly being generated, or the like).

In another embodiment (not illustrated), the scent test screen 412 may be configured to solicit user feedback about the emotional and contextual relevance of the smell. For example, the spectrum of responses depicted on 414-422 ("perfect," "too strong," "too weak," "don't smell target scent," "don't smell anything") may be replaced with emotional indicators for positive, negative, or ambivalent emotional responses. In one example, these responses may be targeting a specific event, where text for 412 may read, for example, "please let us know how this smell feels relative to your current relaxing cross-reality experience" and the feedback responses 414-422 may include an emotive spectrum: "the smell is relaxing and appropriate," "the smell is relaxing but not appropriate," "the smell is not relaxing, but is appropriate," "the smell is not relaxing and not appropriate," or "I don't smell anything." Because other text can be used to solicit user feedback, it should be understood that these examples are illustrative, and therefore should not be construed as being limiting in any way.

The scent test screen 412 also can include a UI control 424 that can be selected to provide custom feedback relating to the scent being generated by the cross-reality device 112 (or other hardware). The scent test screen 412 also can include a UI control 426 that can be selected to exit the scent test screen 412. Thus, for example, the user or other entity can select the UI control 426 to cause the user device 102 to close the scent test screen 412 when the desired information has been obtained via the scent test screen 412, when the user or other entity wishes to close the scent test screen 412 for other reasons, and/or at other times at which the UI control 426 is selected. Because additional or alternative controls can be included in the scent test screen 412, it should be understood that the example embodiment shown in FIG. 4B is illustrative and therefore should not be construed as being limiting in any way.

Figure 5:
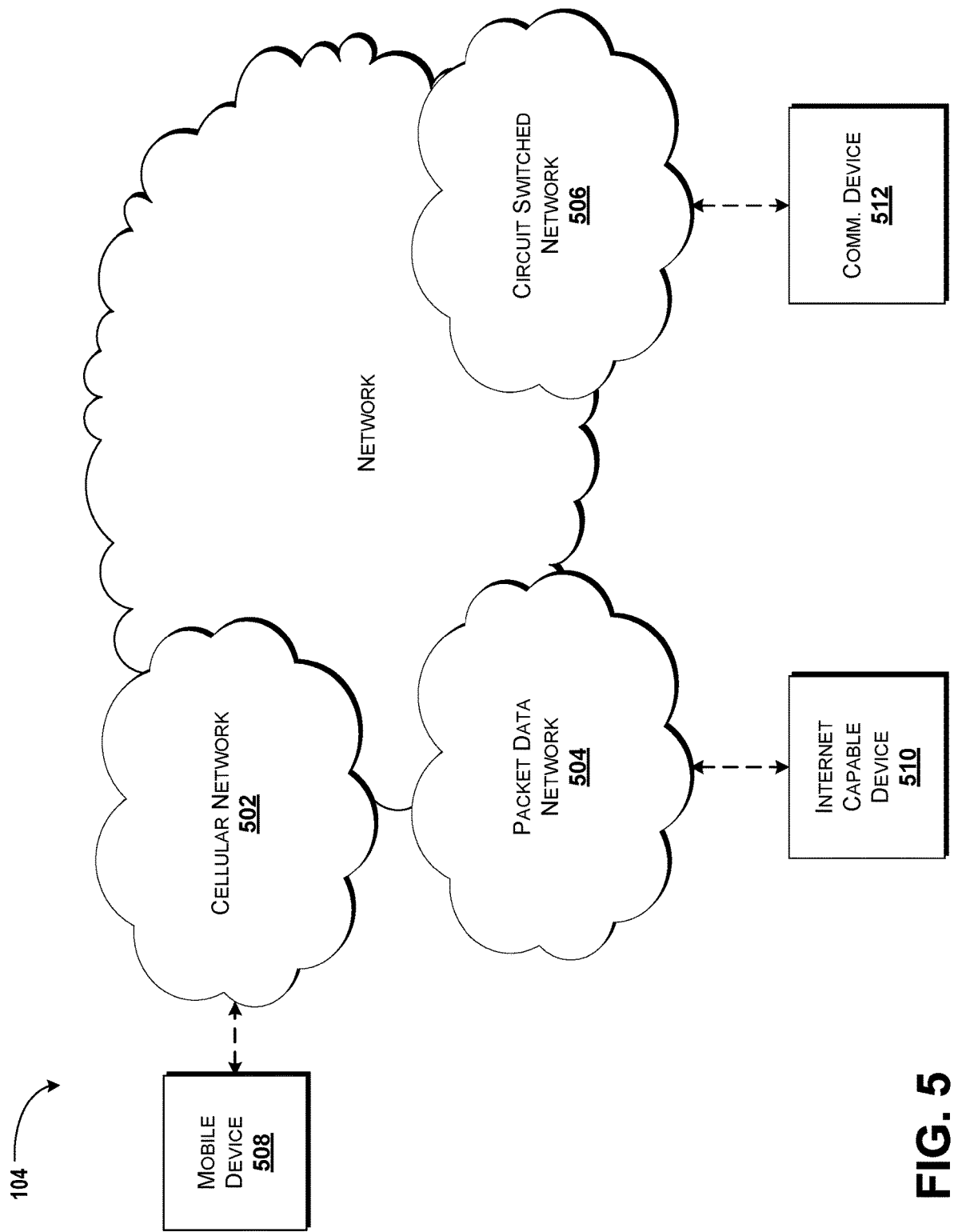
FIG. 5 schematically illustrates a network, according to an illustrative embodiment of the concepts and technologies described herein.

Turning now to FIG. 5, additional details of the network 104 are illustrated, according to an illustrative embodiment. The network 104 includes a cellular network 502, a packet data network 504, for example, the Internet, and a circuit switched network 506, for example, a publicly switched telephone network ("PSTN"). The cellular network 502 includes various components such as, but not limited to, base transceiver stations ("BTSs"), Node-B's or e-Node-B's, base station controllers ("BSCs"), radio network controllers ("RNCs"), mobile switching centers ("MSCs"), mobile management entities ("MMEs"), short message service centers ("SMSCs"), multimedia messaging service centers ("MMSCs"), home location registers ("HLRs"), home subscriber servers ("HSSs"), visitor location registers ("VLRs"), charging platforms, billing platforms, voicemail platforms, GPRS core network components, location service nodes, an IP Multimedia Subsystem ("IMS"), and the like. The cellular network 502 also includes radios and nodes for receiving and transmitting voice, data, and combinations thereof to and from radio transceivers, networks, the packet data network 504, and the circuit switched network 506.

A mobile communications device 508, such as, for example, a cellular telephone, a user equipment, a mobile terminal, a PDA, a laptop computer, a handheld computer, and combinations thereof, can be operatively connected to the cellular network 502. The cellular network 502 can be configured as a 2G GSM network and can provide data communications via GPRS and/or EDGE. Additionally, or alternatively, the cellular network 502 can be configured as a 3G UMTS network and can provide data communications via the HSPA protocol family, for example, HSDPA, EUL (also referred to as HSUPA), and HSPA+. The cellular network 502 also is compatible with 4G mobile communications standards, 5G mobile communications standards, other mobile communications standards, and evolved and future mobile communications standards.

The packet data network 504 includes various devices, for example, servers, computers, databases, and other devices in communication with one another, as is generally known. The packet data network 504 devices are accessible via one or more network links. The servers often store various files that are provided to a requesting device such as, for example, a computer, a terminal, a smartphone, or the like. Typically, the requesting device includes software (a "browser") for executing a web page in a format readable by the browser or other software. Other files and/or data may be accessible via "links" in the retrieved files, as is generally known. In some embodiments, the packet data network 504 includes or is in communication with the Internet. The circuit switched network 506 includes various hardware and software for providing circuit switched communications. The circuit switched network 506 may include, or may be, what is often referred to as a plain old telephone system (POTS). The functionality of a circuit switched network 506 or other circuit-switched network are generally known and will not be described herein in detail.

The illustrated cellular network 502 is shown in communication with the packet data network 504 and a circuit switched network 506, though it should be appreciated that this is not necessarily the case. One or more Internet-capable devices 510, for example, a PC, a laptop, a portable device, or another suitable device, can communicate with one or more cellular networks 502, and devices connected thereto, through the packet data network 504. It also should be appreciated that the Internet-capable device 510 can communicate with the packet data network 504 through the circuit switched network 506, the cellular network 502, and/or via other networks (not illustrated).

As illustrated, a communications device 512, for example, a telephone, facsimile machine, modem, computer, or the like, can be in communication with the circuit switched network 506, and therethrough to the packet data network 504 and/or the cellular network 502. It should be appreciated that the communications device 512 can be an Internet-capable device, and can be substantially similar to the Internet-capable device 510. In the specification, the network 104 is used to refer broadly to any combination of the networks 502, 504, 506. It should be appreciated that substantially all of the functionality described with reference to the network 104 can be performed by the cellular network 502, the packet data network 504, and/or the circuit switched network 506, alone or in combination with other networks, network elements, and the like.

Figure 6:
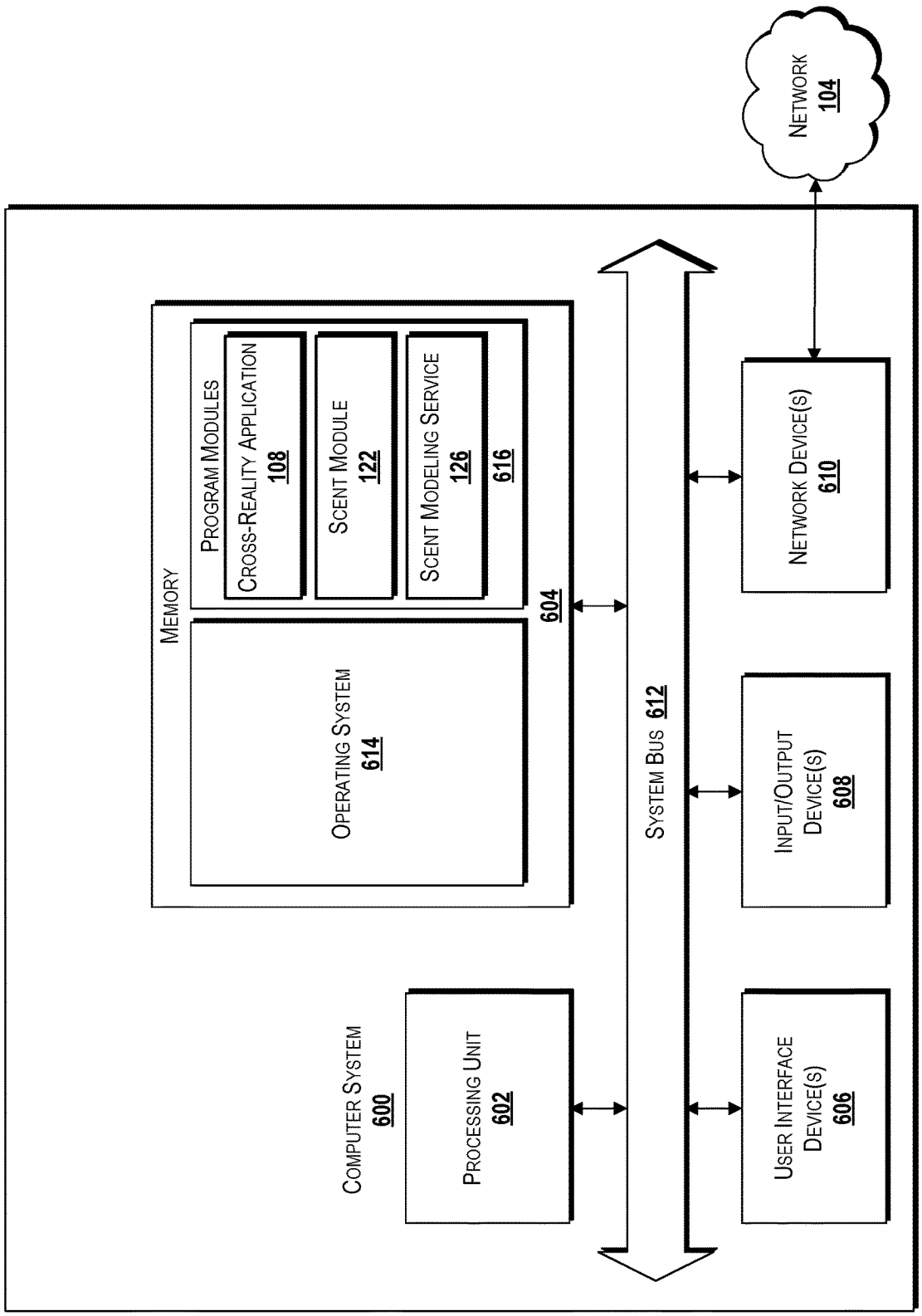
FIG. 6 is a block diagram illustrating an example computer system configured to create scent models and use scent models in cross-reality environments, according to some illustrative embodiments of the concepts and technologies described herein.

FIG. 6 is a block diagram illustrating a computer system 600 configured to provide the functionality described herein for creating scent models and using scent models in cross-reality environments, in accordance with various embodiments of the concepts and technologies disclosed herein. The computer system 600 includes a processing unit 602, a memory 604, one or more user interface devices 606, one or more input/output ("I/O") devices 608, and one or more network devices 610, each of which is operatively connected to a system bus 612. The bus 612 enables bi-directional communication between the processing unit 602, the memory 604, the user interface devices 606, the I/O devices 608, and the network devices 610.

The processing unit 602 may be a standard central processor that performs arithmetic and logical operations, a more specific purpose programmable logic controller ("PLC"), a programmable gate array, or other type of processor known to those skilled in the art and suitable for controlling the operation of the server computer. As used herein, the word "processor" and/or the phrase "processing unit" when used with regard to any architecture or system can include multiple processors or processing units distributed across and/or operating in parallel in a single machine or in multiple machines. Furthermore, processors and/or processing units can be used to support virtual processing environments. Processors and processing units also can include state machines, application-specific integrated circuits ("ASICs"), combinations thereof, or the like. Because processors and/or processing units are generally known, the processors and processing units disclosed herein will not be described in further detail herein.

The memory 604 communicates with the processing unit 602 via the system bus 612. In some embodiments, the memory 604 is operatively connected to a memory controller (not shown) that enables communication with the processing unit 602 via the system bus 612. The memory 604 includes an operating system 614 and one or more program modules 616. The operating system 614 can include, but is not limited to, members of the WINDOWS, WINDOWS CE, and/or WINDOWS MOBILE families of operating systems from MICROSOFT CORPORATION, the LINUX family of operating systems, the SYMBIAN family of operating systems from SYMBIAN LIMITED, the BREW family of operating systems from QUALCOMM CORPORATION, the MAC OS, iOS, and/or LEOPARD families of operating systems from APPLE CORPORATION, the FREEBSD family of operating systems, the SOLARIS family of operating systems from ORACLE CORPORATION, other operating systems, and the like.

The program modules 616 may include various software and/or program modules described herein. In some embodiments, for example, the program modules 616 include the cross-reality application 108, the scent module 122, and/or the scent modeling service 126. These and/or other programs can be embodied in computer-readable media containing instructions that, when executed by the processing unit 602, perform one or more of the methods 200 and 300 described in detail above with respect to FIGS. 2-3 and/or other functionality as illustrated and described herein. It can be appreciated that, at least by virtue of the instructions embodying the methods 200 and 300 and/or other functionality illustrated and described herein being stored in the memory 604 and/or accessed and/or executed by the processing unit 602, the computer system 600 is a special-purpose computing system that can facilitate providing the functionality illustrated and described herein. According to embodiments, the program modules 616 may be embodied in hardware, software, firmware, or any combination thereof. Although not shown in FIG. 6, it should be understood that the memory 604 also can be configured to store the scent models 110, the experience data 120, and/or other data, if desired.

By way of example, and not limitation, computer-readable media may include any available computer storage media or communication media that can be accessed by the computer system 600. Communication media includes computer-readable instructions, data structures, program modules, or other data in a modulated data signal such as a carrier wave or other transport mechanism and includes any delivery media. The term "modulated data signal" means a signal that has one or more of its characteristics changed or set in a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

Computer storage media includes only non-transitory embodiments of computer readable media as illustrated and described herein. Thus, computer storage media can include volatile and non-volatile, removable and non-removable media implemented in any method or technology for storage of information such as computer-readable instructions, data structures, program modules, or other data. Computer storage media includes, but is not limited to, RAM, ROM, Erasable Programmable ROM ("EPROM"), Electrically Erasable Programmable ROM ("EEPROM"), flash memory or other solid state memory technology, CD-ROM, digital versatile disks ("DVD"), or other optical storage, magnetic cassettes, magnetic tape, magnetic disk storage or other magnetic storage devices, or any other medium which can be used to store the desired information and which can be accessed by the computer system 600. In the claims, the phrase "computer storage medium" and variations thereof does not include waves or signals per se and/or communication media.

The user interface devices 606 may include one or more devices with which a user accesses the computer system 600. The user interface devices 606 may include, but are not limited to, computers, servers, personal digital assistants, cellular phones, or any suitable computing devices. The I/O devices 608 enable a user to interface with the program modules 616. In one embodiment, the I/O devices 608 are operatively connected to an I/O controller (not shown) that enables communication with the processing unit 602 via the system bus 612. The I/O devices 608 may include one or more input devices, such as, but not limited to, a keyboard, a mouse, or an electronic stylus. Further, the I/O devices 608 may include one or more output devices, such as, but not limited to, a display screen or a printer.

The network devices 610 enable the computer system 600 to communicate with other networks or remote systems via a network, such as the network 104. Examples of the network devices 610 include, but are not limited to, a modem, a radio frequency ("RF") or infrared ("IR") transceiver, a telephonic interface, a bridge, a router, or a network card. The network 104 may include a wireless network such as, but not limited to, a Wireless Local Area Network ("WLAN") such as a WI-FI network, a Wireless Wide Area Network ("WWAN"), a Wireless Personal Area Network ("WPAN") such as BLUETOOTH, a Wireless Metropolitan Area Network ("WMAN") such as a WiMAX network, or a cellular network. Alternatively, the network 104 may be a wired network such as, but not limited to, a Wide Area Network ("WAN") such as the Internet, a Local Area Network ("LAN") such as the Ethernet, a wired Personal Area Network ("PAN"), or a wired Metropolitan Area Network ("MAN").

Figure 7:
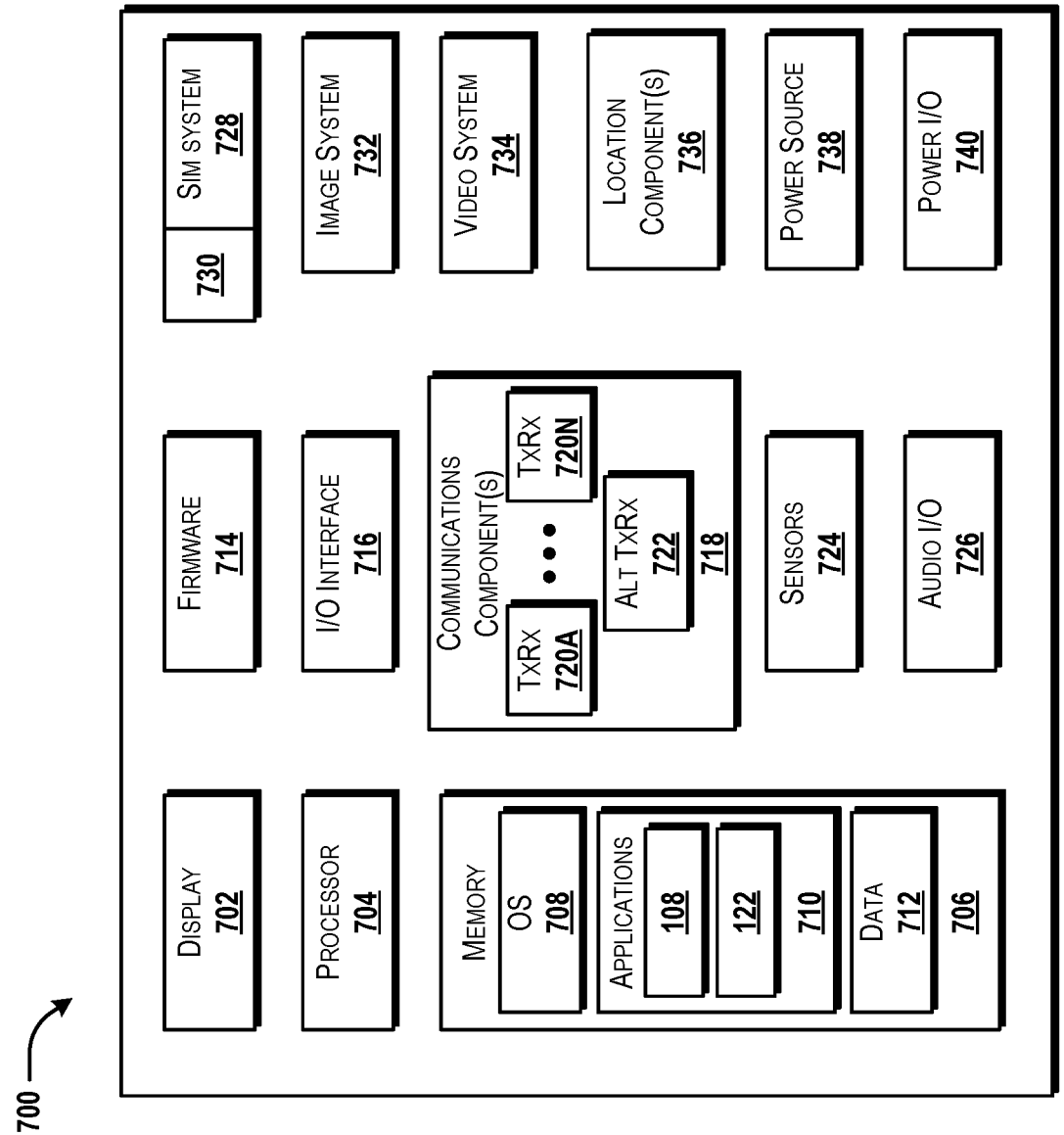
FIG. 7 is a block diagram illustrating an example mobile device configured to create scent models and use scent models in cross-reality environments, according to some illustrative embodiments of the concepts and technologies described herein.

Turning now to FIG. 7, an illustrative mobile device 700 and components thereof will be described. In some embodiments, the user device 102 described above with reference to FIG. 1 can be configured as and/or can have an architecture similar or identical to the mobile device 700 described herein in FIG. 7. It should be understood, however, that the user device 102 may or may not include the functionality described herein with reference to FIG. 7. While connections are not shown between the various components illustrated in FIG. 7, it should be understood that some, none, or all of the components illustrated in FIG. 7 can be configured to interact with one another to carry out various device functions. In some embodiments, the components are arranged so as to communicate via one or more busses (not shown). Thus, it should be understood that FIG. 7 and the following description are intended to provide a general understanding of a suitable environment in which various aspects of embodiments can be implemented, and should not be construed as being limiting in any way.

As illustrated in FIG. 7, the mobile device 700 can include a display 702 for displaying data. According to various embodiments, the display 702 can be configured to display various graphical user interface ("GUI") elements such as, for example, text, images, video, virtual keypads and/or keyboards, messaging data, notification messages, metadata, internet content, device status, time, date, calendar data, device preferences, map and location data, combinations thereof, and/or the like. The mobile device 700 also can include a processor 704 and a memory or other data storage device ("memory") 706. The processor 704 can be configured to process data and/or can execute computer-executable instructions stored in the memory 706. The computer-executable instructions executed by the processor 704 can include, for example, an operating system 708, one or more applications 710 such as the cross-reality application 108, the scent module 122, the scent modeling service 126, other computer-executable instructions stored in a memory 706, or the like. In some embodiments, the applications 710 also can include a UI application (not illustrated in FIG. 7).

The UI application can interface with the operating system 708, such as the operating system 106 shown in FIG. 1, to facilitate user interaction with functionality and/or data stored at the mobile device 700 and/or stored elsewhere. In some embodiments, the operating system 708 can include a member of the SYMBIAN OS family of operating systems from SYMBIAN LIMITED, a member of the WINDOWS MOBILE OS and/or WINDOWS PHONE OS families of operating systems from MICROSOFT CORPORATION, a member of the PALM WEBOS family of operating systems from HEWLETT PACKARD CORPORATION, a member of the BLACKBERRY OS family of operating systems from RESEARCH IN MOTION LIMITED, a member of the IOS family of operating systems from APPLE INC., a member of the ANDROID OS family of operating systems from GOOGLE INC., and/or other operating systems. These operating systems are merely illustrative of some contemplated operating systems that may be used in accordance with various embodiments of the concepts and technologies described herein and therefore should not be construed as being limiting in any way.

The UI application can be executed by the processor 704 to aid a user in entering content, performing setup functions, performing scent tests, entering personalization information, configuring settings, manipulating address book content and/or settings, multimode interaction, interacting with other applications 710, and otherwise facilitating user interaction with the operating system 708, the applications 710, and/or other types or instances of data 712 that can be stored at the mobile device 700. The data 712 can include, for example, the cross-reality application 108, the scent module 122, the scent modeling service 126, and/or other applications or program modules. According to various embodiments, the data 712 can include, for example, presence applications, visual voice mail applications, messaging applications, text-to-speech and speech-to-text applications, add-ons, plug-ins, email applications, music applications, video applications, camera applications, location-based service applications, power conservation applications, game applications, productivity applications, entertainment applications, enterprise applications, combinations thereof, and the like. The applications 710, the data 712, and/or portions thereof can be stored in the memory 706 and/or in a firmware 714, and can be executed by the processor 704.

It can be appreciated that, at least by virtue of storage of the instructions corresponding to the applications 710 and/or other instructions embodying other functionality illustrated and described herein in the memory 706, and/or by virtue of the instructions corresponding to the applications 710 and/or other instructions embodying other functionality illustrated and described herein being accessed and/or executed by the processor 704, the mobile device 700 is a special-purpose mobile device that can facilitate providing the functionality illustrated and described herein. The firmware 714 also can store code for execution during device power up and power down operations. It can be appreciated that the firmware 714 can be stored in a volatile or non-volatile data storage device including, but not limited to, the memory 706 and/or a portion thereof.

The mobile device 700 also can include an input/output ("I/O") interface 716. The I/O interface 716 can be configured to support the input/output of data such as location information, scent testing information, preferences for a scent modeling service 126, feedback, scent and/or smell information, the scent models 110, experience data 120, user information, organization information, presence status information, user IDs, passwords, and application initiation (start-up) requests. In some embodiments, the I/O interface 716 can include a hardwire connection such as a universal serial bus ("USB") port, a mini-USB port, a micro-USB port, an audio jack, a PS2 port, an IEEE 1394 ("FIRE-WIRE") port, a serial port, a parallel port, an Ethernet (RJ45 or RJ48) port, a telephone (RJ11 or the like) port, a proprietary port, combinations thereof, or the like. In some embodiments, the mobile device 700 can be configured to synchronize with another device to transfer content to and/or from the mobile device 700. In some embodiments, the mobile device 700 can be configured to receive updates to one or more of the applications 710 via the I/O interface 716, though this is not necessarily the case. In some embodiments, the I/O interface 716 accepts I/O devices such as keyboards, keypads, mice, interface tethers, printers, plotters, external storage, touch/multi-touch screens, touch pads, trackballs, joysticks, microphones, remote control devices, displays, projectors, medical equipment (e.g., stethoscopes, heart monitors, and other health metric monitors), modems, routers, external power sources, docking stations, combinations thereof, and the like. It should be appreciated that the I/O interface 716 may be used for communications between the mobile device 700 and a network device or local device.

The mobile device 700 also can include a communications component 718. The communications component 718 can be configured to interface with the processor 704 to facilitate wired and/or wireless communications with one or more networks such as the network 104 described herein. In some embodiments, other networks include networks that utilize non-cellular wireless technologies such as WI-FI or WIMAX. In some embodiments, the communications component 718 includes a multimode communications subsystem for facilitating communications via the cellular network and one or more other networks.

The communications component 718, in some embodiments, includes one or more transceivers. The one or more transceivers, if included, can be configured to communicate over the same and/or different wireless technology standards with respect to one another. For example, in some embodiments one or more of the transceivers of the communications component 718 may be configured to communicate using GSM, CDMAONE, CDMA2000, LTE, and various other 2G, 2.5G, 3G, 4G, 5G, and greater generation technology standards. Moreover, the communications component 718 may facilitate communications over various channel access methods (which may or may not be used by the aforementioned standards) including, but not limited to, TDMA, FDMA, W-CDMA, OFDM, SDMA, and the like.

In addition, the communications component 718 may facilitate data communications using GPRS, EDGE, the HSPA protocol family including HSDPA, EUL or otherwise termed HSUPA, HSPA+, and various other current and future wireless data access standards. In the illustrated embodiment, the communications component 718 can include a first transceiver ("TxRx") 720A that can operate in a first communications mode (e.g., GSM). The communications component 718 also can include an $N^{th}$ transceiver ("TxRx") 720N that can operate in a second communications mode relative to the first transceiver 720A (e.g., UMTS). While two transceivers 720A-N(hereinafter collectively and/or generically referred to as "transceivers 720") are shown in FIG. 7, it should be appreciated that less than two, two, and/or more than two transceivers 720 can be included in the communications component 718.

The communications component 718 also can include an alternative transceiver ("Alt TxRx") 722 for supporting other types and/or standards of communications. According to various contemplated embodiments, the alternative transceiver 722 can communicate using various communications technologies such as, for example, WI-FI, WIMAX, BLUETOOTH, infrared, infrared data association ("IRDA"), near field communications ("NFC"), other RF technologies, combinations thereof, and the like. In some embodiments, the communications component 718 also can facilitate reception from terrestrial radio networks, digital satellite radio networks, internet-based radio service networks, combinations thereof, and the like. The communications component 718 can process data from a network such as the Internet, an intranet, a broadband network, a WI-FI hotspot, an Internet service provider ("ISP"), a digital subscriber line ("DSL") provider, a broadband provider, combinations thereof, or the like.

The mobile device 700 also can include one or more sensors 724. The sensors 724 can include temperature sensors, light sensors, air quality sensors, movement sensors, orientation sensors, noise sensors, proximity sensors, or the like. As such, it should be understood that the sensors 724 can include, but are not limited to, accelerometers, magnetometers, gyroscopes, infrared sensors, noise sensors, microphones, combinations thereof, or the like. Additionally, audio capabilities for the mobile device 700 may be provided by an audio I/O component 726. The audio I/O component 726 of the mobile device 700 can include one or more speakers for the output of audio signals, one or more microphones for the collection and/or input of audio signals, and/or other audio input and/or output devices.

The illustrated mobile device 700 also can include a subscriber identity module ("SIM") system 728. The SIM system 728 can include a universal SIM ("USIM"), a universal integrated circuit card ("UICC") and/or other identity devices. The SIM system 728 can include and/or can be connected to or inserted into an interface such as a slot interface 730. In some embodiments, the slot interface 730 can be configured to accept insertion of other identity cards or modules for accessing various types of networks. Additionally, or alternatively, the slot interface 730 can be configured to accept multiple subscriber identity cards. Because other devices and/or modules for identifying users and/or the mobile device 700 are contemplated, it should be understood that these embodiments are illustrative, and should not be construed as being limiting in any way.

The mobile device 700 also can include an image capture and processing system 732 ("image system"). The image system 732 can be configured to capture or otherwise obtain photos, videos, and/or other visual information. As such, the image system 732 can include cameras, lenses, charge-coupled devices ("CCDs"), combinations thereof, or the like. The mobile device 700 may also include a video system 734. The video system 734 can be configured to capture, process, record, modify, and/or store video content. Photos and videos obtained using the image system 732 and the video system 734, respectively, may be added as message content to an MMS message, email message, and sent to another mobile device. The video and/or photo content also can be shared with other devices via various types of data transfers via wired and/or wireless communication devices as described herein.

The mobile device 700 also can include one or more location components 736. The location components 736 can be configured to send and/or receive signals to determine a geographic location of the mobile device 700. According to various embodiments, the location components 736 can send and/or receive signals from global positioning system ("GPS") devices, assisted-GPS ("A-GPS") devices, WI-FI/WIMAX and/or cellular network triangulation data, combinations thereof, and the like. The location component 736 also can be configured to communicate with the communications component 718 to retrieve triangulation data for determining a location of the mobile device 700. In some embodiments, the location component 736 can interface with cellular network nodes, telephone lines, satellites, location transmitters and/or beacons, wireless network transmitters and receivers, combinations thereof, and the like. In some embodiments, the location component 736 can include and/or can communicate with one or more of the sensors 724 such as a compass, an accelerometer, and/or a gyroscope to determine the orientation of the mobile device 700. Using the location component 736, the mobile device 700 can generate and/or receive data to identify its geographic location, or to transmit data used by other devices to determine the location of the mobile device 700. The location component 736 may include multiple components for determining the location and/or orientation of the mobile device 700.

The illustrated mobile device 700 also can include a power source 738. The power source 738 can include one or more batteries, power supplies, power cells, and/or other power subsystems including alternating current ("AC") and/or direct current ("DC") power devices. The power source 738 also can interface with an external power system or charging equipment via a power I/O component 740. Because the mobile device 700 can include additional and/or alternative components, the above embodiment should be understood as being illustrative of one possible operating environment for various embodiments of the concepts and technologies described herein. The described embodiment of the mobile device 700 is illustrative, and should not be construed as being limiting in any way.

FIG. 8 illustrates an illustrative architecture for a cloud computing platform 800 that can be capable of executing the software components described herein for creating scent models and using scent models in cross-reality environments and/or for interacting with the cross-reality application 108, the scent module 122, and/or the scent modeling service 126. Thus, it can be appreciated that in some embodiments of the concepts and technologies disclosed herein, the cloud computing platform 800 illustrated in FIG. 8 can be used to provide the functionality described herein with respect to the user device 102, the cross-reality device 112, and/or the server computer 128.

The cloud computing platform 800 thus may be utilized to execute any aspects of the software components presented herein. Thus, according to various embodiments of the concepts and technologies disclosed herein, the cross-reality application 108, the scent module 122, and/or the scent modeling service 126 can be implemented, at least in part, on or by elements included in the cloud computing platform 800 illustrated and described herein. Those skilled in the art will appreciate that the illustrated cloud computing platform 800 is a simplification of but only one possible implementation of an illustrative cloud computing platform, and as such, the illustrated cloud computing platform 800 should not be construed as being limiting in any way.

In the illustrated embodiment, the cloud computing platform 800 can include a hardware resource layer 802, a virtualization/control layer 804, and a virtual resource layer 806. These layers and/or other layers can be configured to cooperate with each other and/or other elements of a cloud computing platform 800 to perform operations as will be described in detail herein. While connections are shown between some of the components illustrated in FIG. 8, it should be understood that some, none, or all of the components illustrated in FIG. 8 can be configured to interact with one another to carry out various functions described herein. In some embodiments, the components are arranged so as to communicate via one or more networks such as, for example, the network 104 illustrated and described hereinabove (not shown in FIG. 8). Thus, it should be understood that FIG. 8 and the following description are intended to provide a general understanding of a suitable environment in which various aspects of embodiments can be implemented, and should not be construed as being limiting in any way.

The hardware resource layer 802 can provide hardware resources. In the illustrated embodiment, the hardware resources can include one or more compute resources 808, one or more memory resources 810, and one or more other resources 812. The compute resource(s) 808 can include one or more hardware components that can perform computations to process data, and/or to execute computer-executable instructions of one or more application programs, operating systems, services, and/or other software including, but not limited to, the cross-reality application 108 and/or the scent modeling service 126 illustrated and described herein.

According to various embodiments, the compute resources 808 can include one or more central processing units ("CPUs"). The CPUs can be configured with one or more processing cores. In some embodiments, the compute resources 808 can include one or more graphics processing units ("GPUs"). The GPUs can be configured to accelerate operations performed by one or more CPUs, and/or to perform computations to process data, and/or to execute computer-executable instructions of one or more application programs, operating systems, and/or other software that may or may not include instructions that are specifically graphics computations and/or related to graphics computations. In some embodiments, the compute resources 808 can include one or more discrete GPUs. In some other embodiments, the compute resources 808 can include one or more CPU and/or GPU components that can be configured in accordance with a co-processing CPU/GPU computing model. Thus, it can be appreciated that in some embodiments of the compute resources 808, a sequential part of an application can execute on a CPU and a computationally-intensive part of the application can be accelerated by the GPU. It should be understood that this example is illustrative, and therefore should not be construed as being limiting in any way.

In some embodiments, the compute resources 808 also can include one or more system on a chip ("SoC") components. It should be understood that an SoC component can operate in association with one or more other components as illustrated and described herein, for example, one or more of the memory resources 810 and/or one or more of the other resources 812. In some embodiments in which an SoC component is included, the compute resources 808 can be or can include one or more embodiments of the SNAPDRAGON brand family of SoCs, available from QUALCOMM of San Diego, California; one or more embodiment of the TEGRA brand family of SoCs, available from NVIDIA of Santa Clara, California; one or more embodiment of the HUMMINGBIRD brand family of SoCs, available from SAMSUNG of Seoul, South Korea; one or more embodiment of the Open Multimedia Application Platform ("OMAP") family of SoCs, available from TEXAS INSTRUMENTS of Dallas, Texas; one or more customized versions of any of the above SoCs; and/or one or more other brand and/or one or more proprietary SoCs.

The compute resources 808 can be or can include one or more hardware components arranged in accordance with an ARM architecture, available for license from ARM HOLDINGS of Cambridge, United Kingdom. Alternatively, the compute resources 808 can be or can include one or more hardware components arranged in accordance with an x86 architecture, such as an architecture available from INTEL CORPORATION of Mountain View, California, and others. Those skilled in the art will appreciate the implementation of the compute resources 808 can utilize various computation architectures and/or processing architectures. As such, the various example embodiments of the compute resources 808 as mentioned hereinabove should not be construed as being limiting in any way. Rather, implementations of embodiments of the concepts and technologies disclosed herein can be implemented using compute resources 808 having any of the particular computation architecture and/or combination of computation architectures mentioned herein as well as other architectures.

Although not separately illustrated in FIG. 8, it should be understood that the compute resources 808 illustrated and described herein can host and/or execute various services, applications, portals, and/or other functionality illustrated and described herein. Thus, the compute resources 808 can host and/or can execute the cross-reality application 108, the scent modeling service 126, and/or other applications or services illustrated and described herein.

The memory resource(s) 810 can include one or more hardware components that can perform or provide storage operations, including temporary and/or permanent storage operations. In some embodiments, the memory resource(s) 810 can include volatile and/or non-volatile memory implemented in any method or technology for storage of information such as computer-readable instructions, data structures, program modules, or other data disclosed herein. Computer storage media is defined hereinabove and therefore should be understood as including, in various embodiments, random access memory ("RAM"), read-only memory ("ROM"), Erasable Programmable ROM ("EPROM"), Electrically Erasable Programmable ROM ("EEPROM"), flash memory or other solid state memory technology, CD-ROM, digital versatile disks ("DVD"), or other optical storage, magnetic cassettes, magnetic tape, magnetic disk storage or other magnetic storage devices, or any other medium that can be used to store data and that can be accessed by the compute resources 808, subject to the definition of "computer storage media" provided above (e.g., as excluding waves and signals per se and/or communication media as defined in this application).

Although not illustrated in FIG. 8, it should be understood that the memory resources 810 can host or store the various data illustrated and described herein including, but not limited to, the scent model 110, the experience data 120, and/or other data, if desired. It should be understood that this example is illustrative, and therefore should not be construed as being limiting in any way.

The other resource(s) 812 can include any other hardware resources that can be utilized by the compute resources(s) 808 and/or the memory resource(s) 810 to perform operations. The other resource(s) 812 can include one or more input and/or output processors (e.g., a network interface controller and/or a wireless radio), one or more modems, one or more codec chipsets, one or more pipeline processors, one or more fast Fourier transform ("FFT") processors, one or more digital signal processors ("DSPs"), one or more speech synthesizers, combinations thereof, or the like.

The hardware resources operating within the hardware resource layer 802 can be virtualized by one or more virtual machine monitors ("VMMs") 814A-814N (also known as "hypervisors;" hereinafter "VMMs 814"). The VMMs 814 can operate within the virtualization/control layer 804 to manage one or more virtual resources that can reside in the virtual resource layer 806. The VMMs 814 can be or can include software, firmware, and/or hardware that alone or in combination with other software, firmware, and/or hardware, can manage one or more virtual resources operating within the virtual resource layer 806.

The virtual resources operating within the virtual resource layer 806 can include abstractions of at least a portion of the compute resources 808, the memory resources 810, the other resources 812, or any combination thereof. These abstractions are referred to herein as virtual machines ("VMs"). In the illustrated embodiment, the virtual resource layer 806 includes VMs 816A-816N (hereinafter "VMs 816").

Based on the foregoing, it should be appreciated that systems and methods for creating scent models and using scent models in cross-reality environments have been disclosed herein. Although the subject matter presented herein has been described in language specific to computer structural features, methodological and transformative acts, specific computing machinery, and computer-readable media, it is to be understood that the concepts and technologies disclosed herein are not necessarily limited to the specific features, acts, or media described herein. Rather, the specific features, acts and mediums are disclosed as example forms of implementing the concepts and technologies disclosed herein.

The subject matter described above is provided by way of illustration only and should not be construed as limiting. Various modifications and changes may be made to the subject matter described herein without following the example embodiments and applications illustrated and described, and without departing from the true spirit and scope of the embodiments of the concepts and technologies disclosed herein.

The invention claimed is:

1. A system comprising:
 a user device comprising a processor and a scent sensor;
 a cross-reality device that is in communication with the user device, the cross-reality device comprising a scent generator; and
 a memory that stores computer-executable instructions that, when executed by the processor, cause the processor to perform operations comprising
  capturing, at the user device and using the scent sensor, experience data that comprises scent data that defines a scent detected using the scent sensor and context data that defines a context in which the scent was detected, wherein the context comprises a process being performed by the user device when the scent was detected and an environmental condition at the user device when the scent was detected,
  providing, to a scent modeling service, the experience data, wherein the scent modeling service generates a scent model associated with a user of the user device based on the experience data, wherein the scent model represents perceived scents and perceived scent intensities associated with the user, and wherein the scent model associates the perceived scents and the perceived scent intensities with the context,
  obtaining, from the scent modeling service, the scent model, and
  using the scent model to generate cross-reality session data, wherein the cross-reality session data is used in a cross-reality session that is presented by the cross-reality device that is in communication with the user device, wherein the cross-reality session comprises a further context that is similar to the context in which the scent was detected, wherein the cross-reality device generates the cross-reality session using the cross-reality session data obtained from the user device, and wherein the cross-reality device generates a further scent during the cross-reality session based on the scent model and based on the further context.

2. The system of claim 1, wherein the computer-executable instructions, when executed by the processor, cause the processor to perform operations further comprising:
 obtaining feedback relating to the further scent that was generated during the cross-reality session;
 in response to a determination that the scent model is to be updated based on the feedback, sending, to the scent modeling service, feedback data that describes the feedback; and
 receiving, from the scent modeling service, an updated scent model.

3. The system of claim 1, wherein the experience data further comprises test data that defines a plurality of scents detected during a scent test, and wherein the test data defines, for each scent of the plurality of scents, an identification of the respective scent and an intensity of the respective scent.

4. The system of claim 1, wherein the context data further defines a geographical location at which the scent was detected.

5. The system of claim 4, wherein the context data further defines an activity with which the user device was involved when the scent was detected.

6. The system of claim 1, wherein the experience data further comprises preference data that defines user likes and dislikes, wherein the preference data defines a first plurality of scents that should not be presented in the cross-reality session and a second plurality of scents that should be presented in the cross-reality session.

7. The system of claim 1, wherein the scent model comprises a data structure that defines a plurality of scents and a plurality of scent intensities, wherein the plurality of scent intensities are defined in parts per million.

8. A method comprising:

capturing, at a user device comprising a processor and a scent sensor, experience data comprising scent data that defines a scent detected using the scent sensor and context data that defines a context in which the scent was detected, wherein the context comprises a process being performed by the user device when the scent was detected and an environmental condition at the user device when the scent was detected;

providing, by the processor and to a scent modeling service, the experience data, wherein the scent modeling service generates a scent model associated with a user of the user device based on the experience data, wherein the scent model represents perceived scents and perceived scent intensities for the user, and wherein the scent model associates the perceived scents and the perceives perceived scent intensities with the context;

obtaining, by the processor and from the scent modeling service, the scent model; and using, by the processor, the scent model to generate cross-reality session data, wherein the cross-reality session data is used in a cross-reality session that is presented by a cross-reality device that is in communication with the user device, wherein the cross-reality session comprises a further context that is similar to the context in which the scent was detected, wherein the cross-reality device comprises a scent generator, wherein the cross-reality device generates the cross-reality session using the cross-reality session data obtained from the user device, and wherein the cross-reality device generates a further scent during the cross-reality session based on the scent model and based on the further context.

9. The method of claim 8, further comprising:

obtaining feedback relating to the further scent that was generated during the cross-reality session;

in response to a determination that the scent model is to be updated based on the feedback, sending, to the scent modeling service, feedback data that describes the feedback; and receiving, from the scent modeling service, an updated scent model.

10. The method of claim 8, wherein the experience data further comprises test data that defines a plurality of scents detected during a scent test, and wherein the test data defines, for each scent of the plurality of scents, an identification of the respective scent and an intensity of the respective scent.

11. The method of claim 8, wherein the context data further defines a geographical location at which the scent was detected.

12. The method of claim 11, wherein the context data further defines an activity with which the user device was involved when the scent was detected.

13. The method of claim 8, wherein the experience data further comprises preference data that defines user likes and dislikes, wherein the preference data defines a first plurality of scents that should not be presented in the cross-reality session and a second plurality of scents that should be presented in the cross-reality session.

14. A computer storage medium having computer-executable instructions stored thereon that, when executed by a processor, cause the processor to perform operations comprising:

capturing, at a user device comprising a scent sensor, experience data comprising scent data that defines a scent detected using the scent sensor and context data that defines a context in which the scent was detected, wherein the context comprises a process being performed by the user device when the scent was detected and an environmental condition at the user device when the scent was detected;

providing, to a scent modeling service, the experience data, wherein the scent modeling service generates a scent model associated with a user of the user device based on the experience data, wherein the scent model represents perceived scents and perceived scent intensities for the user, and wherein the scent model associates the perceived scents and the perceives perceived scent intensities with the context;

obtaining, from the scent modeling service, the scent model; and using the scent model to generate cross-reality session data, wherein the cross-reality session data is used in a cross-reality session that is presented by a cross-reality device that is in communication with the user device, wherein the cross-reality session comprises a further context that is similar to the context in which the scent was detected, wherein the cross-reality device comprises a scent generator, wherein the cross-reality device generates the cross-reality session using the cross-reality session data obtained from the user device, and wherein the cross-reality device generates a further scent during the cross-reality session based on the scent model and based on the further context.

15. The computer storage medium of claim 14, wherein the computer-executable instructions, when executed by the processor, cause the processor to perform operations further comprising:

obtaining feedback relating to the further scent that was generated during the cross-reality session;

in response to a determination that the scent model is to be updated based on the feedback, sending, to the scent modeling service, feedback data that describes the feedback; and receiving, from the scent modeling service, an updated scent model.

16. The computer storage medium of claim 14, wherein the experience data further comprises test data that defines a plurality of scents detected during a scent test, and wherein the test data defines, for each scent of the plurality of scents, an identification of the respective scent and an intensity of the respective scent.

17. The computer storage medium of claim 14, wherein the context data further defines a geographical location at which the scent was detected.

18. The computer storage medium of claim 17, wherein the context data further defines an activity with which the user device was involved when the scent was detected.

19. The computer storage medium of claim 14, wherein the experience data further comprises preference data that defines user likes and dislikes, wherein the preference data defines a first plurality of scents that should not be presented in the cross-reality session and a second plurality of scents that should be presented in the cross-reality session.

20. The computer storage medium of claim 14, wherein the scent model comprises a data structure that defines a plurality of scents and a plurality of scent intensities, wherein the plurality of scent intensities are defined in parts per million.

* * * * *